United States Patent
Jeong

(10) Patent No.: US 9,189,705 B2
(45) Date of Patent: Nov. 17, 2015

(54) PHASE-CONTROLLED MODEL-BASED OVERLAY MEASUREMENT SYSTEMS AND METHODS

(71) Applicant: JSMSW Technology LLC, Walnut Creek, CA (US)

(72) Inventor: Hwan J. Jeong, Los Altos, CA (US)

(73) Assignee: JSMSW Technology LLC, Walnut Creek, CA (US)

( * ) Notice: Subject to any disclaimer, the term of this patent is extended or adjusted under 35 U.S.C. 154(b) by 24 days.

(21) Appl. No.: 14/328,783

(22) Filed: Jul. 11, 2014

(65) Prior Publication Data

US 2015/0043803 A1     Feb. 12, 2015

Related U.S. Application Data

(60) Provisional application No. 61/863,469, filed on Aug. 8, 2013.

(51) Int. Cl.

| | |
|---|---|
| *G06K 9/00* | (2006.01) |
| *G06K 9/62* | (2006.01) |
| *G06T 7/00* | (2006.01) |
| *G06K 9/74* | (2006.01) |
| *G03F 7/20* | (2006.01) |
| *G01N 21/956* | (2006.01) |

(52) U.S. Cl.
CPC .......... *G06K 9/6202* (2013.01); *G03F 7/70633* (2013.01); *G06K 9/74* (2013.01); *G06T 7/001* (2013.01); *G01N 21/956* (2013.01); *G06T 2207/30148* (2013.01)

(58) Field of Classification Search
CPC ... G03F 7/70633; G03F 9/7084; G03F 1/144; G06T 7/0004; G06T 2207/30148; G06K 9/6202; G06K 9/74
USPC .......................................... 382/149, 151, 147
See application file for complete search history.

(56) References Cited

U.S. PATENT DOCUMENTS

| | | | |
|---|---|---|---|
| 6,937,344 | B2 | 8/2005 | Monshouwer et al. |
| 7,061,615 | B1 | 6/2006 | Lowe-Webb |
| 7,170,604 | B2 | 1/2007 | Sezginer et al. |
| 7,193,715 | B2 | 3/2007 | Smedt et al. |
| 7,277,185 | B2 | 10/2007 | Monshouwer et al. |
| 7,379,184 | B2 | 5/2008 | Smith et al. |
| 7,477,396 | B2 | 1/2009 | Smith et al. |
| 7,582,538 | B2 | 9/2009 | Lu et al. |
| 7,651,825 | B2 | 1/2010 | Van Bilsen |
| 7,656,518 | B2 | 2/2010 | Den Boef et al. |
| 7,704,850 | B2 | 4/2010 | Dusa et al. |
| 7,763,403 | B2 | 7/2010 | Van Bilsen |

(Continued)

OTHER PUBLICATIONS

Handbook of Optics vol. II, Second Edition, McGraw-Hill, Inc, 1995, pp. 13.15-13.18.

(Continued)

*Primary Examiner* — Nirav G Patel
*Assistant Examiner* — Shaghayegh Azima
(74) *Attorney, Agent, or Firm* — Opticus IP Law PLLC

(57) ABSTRACT

Overlay measurement systems and methods are disclosed that control the relative phase between the scattered and specular components of light to amplify weak optical signals before detection. The systems and methods utilize model-based regressional image processing to determine overlay errors accurately even in the presence of inter-pattern interference.

21 Claims, 14 Drawing Sheets

(56) References Cited

U.S. PATENT DOCUMENTS

| | | | |
|---|---|---|---|
| 7,786,477 B2 | 8/2010 | Dusa et al. | |
| 7,791,732 B2 | 9/2010 | Den Boef et al. | |
| 7,808,643 B2 | 10/2010 | Smith et al. | |
| 7,864,334 B2 * | 1/2011 | Jeong | G01N 21/45 356/239.7 |
| 7,986,412 B2 | 7/2011 | Jeong | |
| 7,992,115 B2 | 8/2011 | Van Der Heijden et al. | |
| 8,107,079 B2 | 1/2012 | Ausschnitt et al. | |
| 8,339,595 B2 | 12/2012 | Den Boef | |
| 8,339,605 B2 | 12/2012 | Ausschnitt et al. | |
| 8,363,220 B2 | 1/2013 | Coene et al. | |
| 8,441,639 B2 | 5/2013 | Kandel et al. | |
| 2011/0141450 A1 * | 6/2011 | Megens et al. | G03F 7/70466 355/75 |
| 2011/0170091 A1 | 7/2011 | Chang et al. | |
| 2011/0188020 A1 | 8/2011 | Den Boef | |
| 2011/0238365 A1 | 9/2011 | Li et al. | |
| 2012/0153281 A1 | 6/2012 | Ghinovker | |
| 2012/0206729 A1 | 8/2012 | Seligson et al. | |
| 2012/0224176 A1 | 9/2012 | Hammond | |
| 2013/0039460 A1 | 2/2013 | Levy et al. | |
| 2013/0044331 A1 | 2/2013 | Manassen et al. | |
| 2013/0054186 A1 | 2/2013 | Den Boef | |
| 2013/0084655 A1 | 4/2013 | Yue et al. | |
| 2013/0155406 A1 | 6/2013 | Den Boef | |
| 2013/0208279 A1 | 8/2013 | Smith | |
| 2013/0278942 A1 | 10/2013 | Jeong at al. | |

OTHER PUBLICATIONS

H. Kadono, M. Ogusu, S. Toyooka "Phase shifting common path interferometer using a liquid-crystal phase modulator" Optics Communications 110 (1994) pp. 391-400.

Kenneth F. Hulme "Oblique-Cut Longitudinal Electro-optic Modulators", IEEE Journal of Quantum Electronics, vol. QE-7, No. 6, Jun. 1971.

"Numerical Recipes in C," by William H. Press, Saul A. Teukolsky, William T. Vettering and Brian P. Flannery, Cambridge University Press, 1992, pp. 681-685.

* cited by examiner

PHASE-CONTROLLED MODEL-BASED OVERLAY MEASUREMENT SYSTEMS AND METHODS

CLAIM OF PRIORITY

This application claims priority from U.S. Patent Application Ser. No. 61/863,469, filed on Aug. 8, 2013, and which is incorporated by reference herein.

FIELD

This disclosure relates to an optical overlay measurement system, and in particular, relates to systems and methods that employ a phase-controlled optical system for imaging and a model-based regression method for image processing to measure overlay errors precisely, even when the overlay targets are substantially smaller than those currently in use and are surrounded by other patterns.

All documents cited herein are incorporated by reference herein.

BACKGROUND

Most fine structured devices such as integrated circuit chips, microelectromechanical devices, etc. are made of multiple layers of precisely aligned circuit or mechanical patterns. The patterns are usually formed through multiple high precision lithography steps during manufacturing where most patterns are required to be aligned precisely with respect to each other. However, even with best systems and efforts, some amount of lateral misalignment between different patterns is unavoidable. Overlay error is the lateral misalignment between different patterns or targets.

Traditionally, overlay error has referred to the alignment error between successive device layers, which will be called between-layer overlay error herein. However, in some cases such as double- or multi-patterning lithography, overlay error may refer to the lateral misalignment between different patterns in the same layer. This will be called single- or within-layer overlay error herein.

Currently, controlling overlay error is one of the most difficult tasks in semiconductor manufacturing because of the ever shrinking design rules and the complexity in modern manufacturing processes. Because overlay error can affect yield, device performance and reliability, it must be measured precisely. Overlay error can be measured in many different ways. However, in most cases, overlay error is measured optically by capturing the image of specially designed alignment marks called overlay targets and processing the image with a computer. Optical measurement is preferred because it is non-destructive and fast.

The overlay we are interested in is in the functional pattern areas. Unfortunately, optical overlay measurement systems can rarely measure the overlay of functional patterns directly because most of the functional patterns are too fine to be resolved by optical systems. Optical overlay measurement systems usually measure the overlay of functional patterns indirectly using a special non-functional pattern called an overlay target or simply a target. Overlay targets are usually made much coarser than the functional patterns in order to be resolved by optical systems. Optical overlay measurement systems measure the overlay error in the target area and make the assumption that the overlay error in the functional pattern area is the same or at least well correlated with the overlay error in the target area.

Because of the indirectness of the measurement, it is very important to have a good correlation between the two overlay measurements, the functional pattern overlay and the target overlay. In order to have a good correlation between the two overlays, we need to bind the overlay targets to the functional patterns tightly. Their tight binding is commonly achieved by including overlay targets as a part of the pattern design and by printing both the functional patterns and the targets at the same time. This kind of same time design and printing of both functional patterns and targets assures a good correlation between the overlay error measured in the functional pattern area and the overlay error measured in the target area.

When targets are printed, targets belonging to different process layers are printed in the same area on wafer in order to facilitate an accurate measurement of overlay errors. The imaging system takes a picture of all the individual targets in a single image. Thus, an overlay target viewed by an overlay measurement system is not a single target but a group of individual targets, which will be called a target set herein. Thus, a target set is different from an individual target. However, a target set will also be called a target herein whenever the context makes its meaning clear. The measured overlay error is the lateral offset or misalignment between different individual targets printed in the same area. In order to facilitate an accurate overlay measurement, the individual targets are usually printed with no or little overlap with each other even if they are placed in the same area. Thus, all individual targets are usually well distinguishable in the image. A target set usually contains two individual targets. However, it can contain more than two individual targets. In an example, the target area is 100 $\mu m^2$ or less.

Currently, two optical technologies are being used for optical overlay measurement. One is an image-based technology and the other is a diffraction-based technology. Image-based technology takes an image of a target set and processes the image based on intensity slopes to determine the overlay error. Diffraction-based technology uses multiple targets each of which is made of two interleaving gratings. It does not resolve individual grating lines but measures the variation of diffraction efficiency caused by the offset variation between the interleaved gratings. The variation of offset between the two interleaved gratings is the overlay error that needs to be determined.

Diffraction-based overlay measurement systems were developed to achieve higher measurement accuracy than image-based systems. However, these systems have several drawbacks such as a requirement for multiple targets, inflexible target design, complicated system calibration, higher cost, etc. Especially, multiple diffraction targets require a relatively large clear area on the wafer to print all the targets. This makes this technology difficult to employ in many important applications such as in-die overlay measurement where large clear areas for target printing are not available.

The existing image-based overlay measurement systems are reliable and robust. However, they have many critical drawbacks such as requiring large targets, poor handling of weak overlay signals, shallow depth of focus, severe influence from patterns around the target and also from imaging system aberrations, etc. Therefore, the existing image-based overlay measurement systems are not suitable for the future applications most of which require small targets, good handling of weak signals, good filtering of detrimental interferences or influences, etc.

SUMMARY

An aspect of the disclosure is a method of measuring an overlay error between first and second targets having respective actual first target parameters and actual second target parameters and that are respectively associated with first and second patterns that surround the first and second targets and that have respective actual first pattern parameters and actual second pattern parameters. The method includes: a) illuminating the first and second targets to generate a scattered light component and a specular light component having a relative phase; b) using an imaging system having an image plane, capturing the scattered and specular light components at the image plane to form at least three images, wherein the relative phase is different for the at least three images; c) performing an analytical regression to determine from the at least three images a complex amplitude of an optical field of the scattered light component at the image plane; d) using the complex amplitude of the optical field of the scattered light component to obtain estimated first and second target parameters and estimated first and second pattern parameters; e) performing a first numerical regression using an image model of the imaging system, including inputting into the image model the estimated first and second target parameters and the estimated first and second pattern parameters to generate a modeled image, wherein the first numerical regression iteratively compares the modeled image to the measured image and modifies the estimated first and second target parameters and estimated first and second pattern parameters to minimize a difference between the modeled image and the measured image to determine the actual first and second target parameters and the actual first and second pattern parameters; f) determining an optimum phase shift from the actual first and second target parameters; g) capturing an image of the first and second targets using the optimum phase; and h) performing a second numerical regression using the image model and the image captured in act g) to determine a relative position between the first and second targets that defines the overlay error.

Another aspect of the disclosure is a method of measuring an overlay error between first and second targets respectively surrounded by first and second patterns. The method includes: a) using an imaging system having an image plane, capturing at the image plane three images, with each image based on a scattered light component and a specular light component from the first and second targets, wherein for each image the scattered and specular light components have a relative phase, and wherein the relative phase is different for the three images; b) using the three images to define a complex amplitude of the optical field of the scattered light component; c) using the complex amplitude of the optical field of the scattered light component to obtain estimated: i) first target parameters; ii) second target parameters; iii) first pattern parameters; and iv) second pattern parameters; d) using an image model of the imaging system to generate a modeled image based on the estimated first target parameters, the estimated second target parameters, the estimated first pattern parameters, and the estimated second pattern parameters; e) determining actual first target parameters, actual second target parameters, actual first pattern parameters, and actual second pattern parameters that minimize a difference between the modeled image and the measured image; g) capturing an image of the first and second targets and the first and second patterns using the imaging system configured to impart the optimum relative phase; and h) determining a relative position between the first and second targets that defines the overlay error using the image model and the image captured in act g).

Another aspect of the disclosure is a method of measuring an overlay error between first and second targets having respective actual first target parameters and actual second target parameters and that are respectively associated with first and second patterns having respective actual first pattern parameters and actual second pattern parameters. The method includes: a) illuminating the first and second targets to generate a scattered light component and a specular light component having a relative phase; b) using an imaging system having an image plane, capturing at the image plane at least three images of the combined scattered and specular light components, wherein the relative phase is different for the at least three images; c) performing an analytical regression to determine from the at least three images a complex amplitude of an optical field of the scattered light component at the image plane; d) using the complex amplitude of the optical field of the scattered light component to obtain estimated first and second target parameters; and estimated first and second pattern parameters; e) performing a first numerical regression using an image model that takes into account the imaging system characteristics to approximate the image formed in the imaging system, including inputting into the image model the estimated first and second target parameters and the estimated first and second pattern parameters to generate a modeled image, wherein the first numerical regression iteratively compares the modeled image to the measured image and modifies the estimated first and estimated second target parameters and estimated first and estimated second pattern parameters to minimize a difference between the modeled image and the measured image to determine actual first and second target parameters and the actual first and second pattern parameters; f) capturing an image of the first and second targets and first and second patterns using the imaging system configured to block the specular component; and g) performing a second numerical regression using the image model and the image captured in act f) to determine a relative position between the first and second targets that defines the overlay error.

Another aspect of the disclosure is a method of measuring an overlay error between first and second targets having respective actual first target parameters and actual second target parameters and that are respectively associated with first and second patterns that surround the first and second targets and that have respective actual first pattern parameters and actual second pattern parameters. The method includes: a) illuminating the first and second targets to generate a scattered light component; b) using an imaging system having an image plane, capturing at the image plane an image of the scattered component by blocking the specular component; c) estimating the complex amplitude of an optical field of the scattered light component at the image plane; d) using the complex amplitude of the optical field of the scattered light component to obtain estimated first and second target parameters and estimated first and second pattern parameters; e) performing a first numerical regression using an image model of the imaging system, including inputting into the image model the estimated first and second target parameters and the estimated first and second pattern parameters to generate a modeled image, wherein the first numerical regression iteratively compares the modeled image to the measured image and modifies the estimated first and second target parameters and estimated first and second pattern parameters to minimize a difference between the modeled image and the measured image to determine the actual first and second target parameters and the actual first and second pattern parameters; and f) performing a second numerical regression using the image model and the image captured in act b) to determine a relative position between the first and second targets that defines the overlay error.

BRIEF DESCRIPTION OF THE DRAWINGS

The inventive body of work will be readily understood by referring to the following detailed description, in conjunction with the accompanying drawings, in which.

DETAILED DESCRIPTION

Figure 1A:
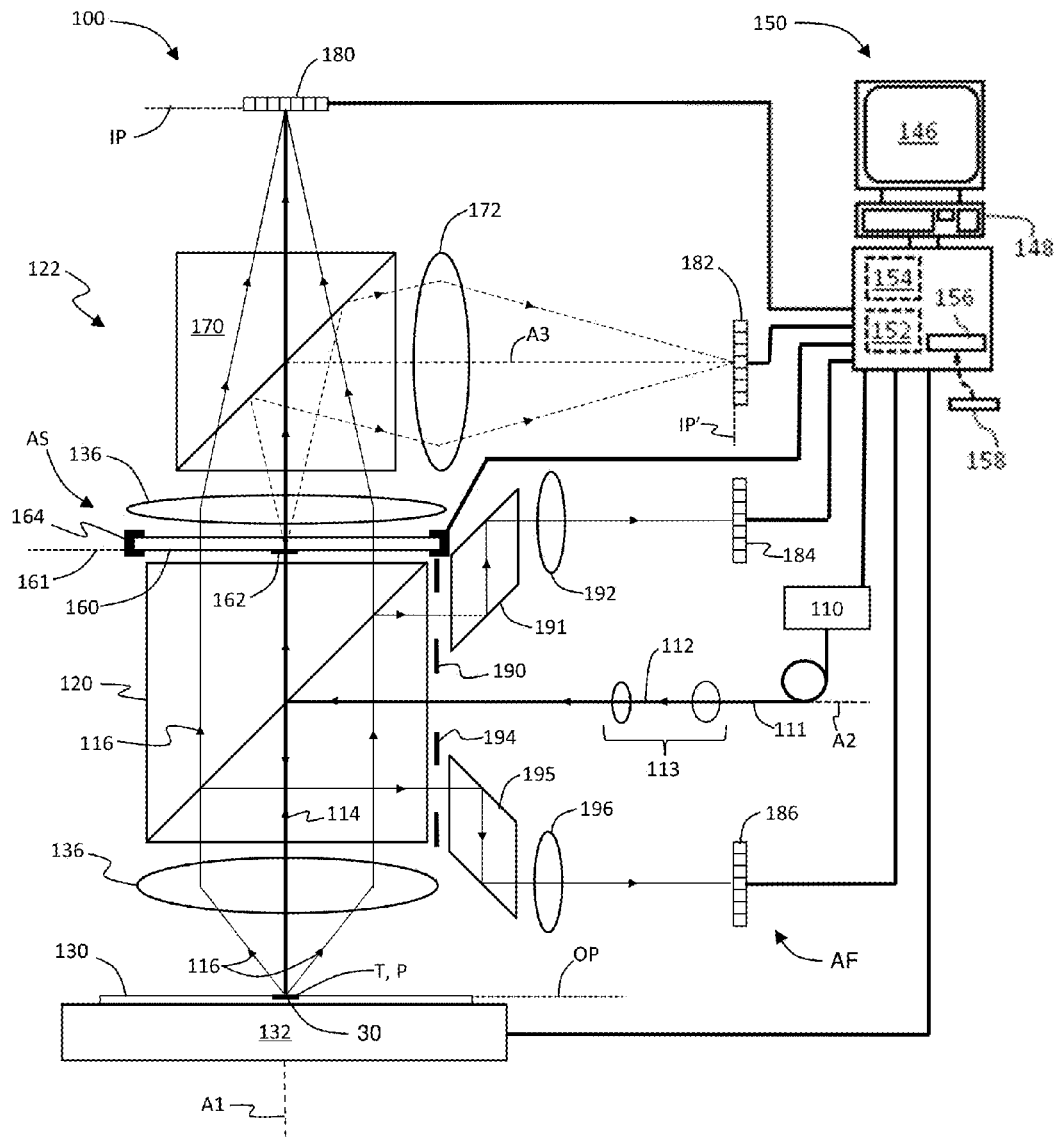
FIG. 1A is a schematic diagram of an example embodiment of an optical overlay measurement system according to the disclosure.

A detailed description of the inventive body of work is provided below. While example embodiments are described, it should be understood that the inventive body of this work is not limited to any one embodiment, but instead encompasses numerous alternatives, modifications, and equivalents, as well as combinations of features from the different embodiments.

In addition, while numerous specific details are set forth in the following description in order to provide a thorough understanding of the inventive body of work, some embodiments can be practiced without some or all of these details. Moreover, for the purpose of clarity, certain technical material that is known in the related art has not been described in detail in order to avoid unnecessarily obscuring the inventive body of work.

The claims as set forth below are incorporated into and constitute part of this detailed description.

Disclosed herein is a general-purpose optical overlay measurement system. Therefore, the disclosure can be applied to any kind of overlay measurement. However, at this moment of time, the main application of the disclosure is expected to be overlay measurement on semiconductor wafers. Therefore, the majority of the description of the disclosure will be about the overlay measurement on semiconductor wafers. However, it is important that the application of the disclosure is not limited to the examples of application presented herein. The scope of the disclosure should not be defined or limited by the examples presented herein. The following description of the disclosure will illustrate the system configuration first and then explain the new image processing method.

FIG. 1 is a schematic diagram of an example optical overlay system ("system") 100 according to the disclosure. System 100 includes a light source 110 operably arranged relative to a first beam splitter 120 disposed along an axis A1 and that generates a light beam 112 of wavelength λ that travels along an axis A2 that intersects optical axis A1 at the beam splitter. Beam splitter 120 is part of an imaging system 122 that includes an object plane OP, an image plane IP and an aperture stop AS. A sample 130 resides at object plane OP and is supported by a sample positioning system (e.g., stage) 132. Sample 30 includes at one or more targets T and one or more patterns P, which are discussed in greater detail below.

In an example, light beam 112 travels through a beam-conditioning optical system 113 arranged along optical axis A2. In an example, beam-conditioning optical system 113 is configured to operate in combination with one or more other optical elements to collimate light beam 112, as discussed below.

Imaging system 122 includes one or more optical elements 136 and a phase-shifting plate 160 supported by an adjustable support member 164, which in an example is a mechanical carriage. Phase-shifting plate includes a phase-shifter 162 that lies along optical axis A1. Imaging system 122 includes a second beam splitter 170 and a first detector 180 also arranged along axis A1 and at image plane IP. Imaging system 122 also includes a second detector 182 arranged along an optical axis A1 that intersects optical axis A1 at the second beam splitter. A relay optical system 172 resides between the second beam splitter 170 and second detector 182. The relay optical system 172 and defines a second image plane IP' at which the second detector 182 resides.

System 100 also includes an autofocus system AF as described in greater detail below. Autofocus system AF includes detectors 184 and 186.

System 100 includes a controller 150 operably connected to light source 110, detectors 180, 182, 184 and 186, and to adjustable support member 164. In an example, controller 150 can be computer, micro-controller or like machine, that is adapted (e.g., via instructions such as software embodied in a computer-readable or machine-readable medium) to control the operation of the various components of the system. Controller 150 is configured to control the operation of system 100 and includes a processing unit ("signal processor") 152, which is electrically connected to detectors 180, 182, 184 and 186, and is adapted to receive and process the digitized raw electronic signal therefrom to extract overlay error and other useful information as will be described in greater detail below. In an example embodiment, signal processor 152 can be made of a single processor or multiple processors depending on the processing capacity required. As used herein, the term "electronic or electrical signal" includes both analog and digital representations of physical quantities and other information.

Signal processor 152 is or includes any processor or device capable of executing a series of software instructions and may include, without limitation, a general or special-purpose microprocessor, finite state machine, controller, computer, central-processing unit (CPU), graphical-processing unit (GPU), massively parallel processor, field-programmable gate array (FPGA), or digital signal processor.

Memory unit ("memory") 154 is operably coupled to signal processor 152. As used herein, the term "memory" refers to any processor-readable medium, including but not limited to RAM, ROM, EPROM, PROM, EEPROM, flash memory, floppy disk, hard disk, SSD (solid-state drive), CD-ROM, DVD, blue ray disk or the like, on which may be stored a series of instructions executable by signal processor 152 or data to be used by or generated by signal processor 152. In an example embodiment, controller 150 includes a port or drive 156 adapted to accommodate a removable processor-readable medium 158, such as CD-ROM, DVD, blue ray disk, memory stick or like storage medium.

The optical overlay measurement methods described herein may be implemented in various embodiments in a machine-readable medium (e.g., memory 154) comprising machine readable instructions (e.g., computer programs and/or software modules) for causing controller 150 to perform the methods and the controlling operations for operating system 100. In an example embodiment, the computer programs run on signal processor 152 might reside in memory 154, and may be transferred to main memory from permanent storage via disk drive or port 156 when stored on removable media 158, or via a network connection or modem connection when stored outside of controller 150, or via other types of computer or machine-readable media from which it can be read and utilized.

The computer programs and/or software modules may comprise multiple modules or objects to perform the various methods of the present disclosure, and control the operation and function of the various components in system 100. The type of computer programming languages used for the code may vary between procedural code-type languages to object-oriented languages. The files or objects need not have a one-to-one correspondence to the modules or method steps described depending on the desires of the programmer. Further, the method and apparatus may comprise combinations of software, hardware and firmware. Firmware can be downloaded into signal processor 152 for implementing the various example embodiments of the disclosure.

Controller 150 also optionally includes a display unit 146 that can be used to display information using a wide variety of alphanumeric and graphical representations. For example, display unit 146 is useful for displaying raw signals, processed signals, regressed model images, resulting overlay errors, optical properties of target and surrounding patterns, etc. Controller 150 also optionally includes a data-entry device 148, such as a keyboard, that allows an operator of system 100 to input information into controller 150 to control the operation of system 100.

In an example embodiment, controller 150 is operably connected to or is part of the sensor systems. Controller 150 is also operably connected to a sample positioning system 132 for positioning the sample, and phase control mechanism 164 for changing the phase. Controller 150 is shown only in system 100 of FIG. 1A for ease of illustration, however it can be included in all example embodiments described herein.

In the general operation of system 100, light source 100 emits a light beam 112 that travels along axis A2 to the first beam splitter 120. In an example, light beam 112 is carried by an optical fiber 111. The light beam 112 is directed by the first beam splitter 120 through optical element 136 to illuminate sample 130. The illumination of sample 130 from light beam 112 covers the whole field of view of the imaging system. The illumination beam 112 is usually collimated at the sample 130, which contains an overlay target and other patterns around the target within the field of view of the imaging system. These are discussed in greater detail below. The sample 30 resides in an object plane OP of imaging system 122 and its position can be adjusted by sample positioning system 132 to ensure proper placement. Therefore, the sample 30 will also be called the object herein.

Also, the object plane OP of the optical system will also be called sample plane herein. In other words, the two words, sample and object, will be used interchangeably herein.

All the patterns P existing in the neighborhood of a corresponding target T and will be called neighboring or surrounding patterns herein. Most of the surrounding patterns perform one or more functions in their final product. Therefore, the surrounding or neighboring patterns P will also be called functional patterns herein. Target T is a special non-functional pattern as explained previously. However, there is no fundamental difference between target T and surrounding patterns P. Therefore, target T will frequently be considered as just another pattern P or a part of the whole pattern. Thus, the whole pattern P in the field of view of the imaging system 122 is usually composed of target set and surrounding patterns. The whole pattern P will be called "pattern set" herein. It will also be called just "pattern" when the context makes its meaning clear.

The patterns P in the sample 30 scatter (or diffract) a portion of the illuminating light from light beam 112 and also directly reflect some portion of the illumination light. The directly reflected light is denoted 114 and the scattered light is denoted 116.

There is no fundamental difference between scattering and diffraction of light. Therefore, the terms "scattering" and "diffraction" are used synonymously herein. Direct reflection of light means a minor-like reflection without any scattering herein. The directly reflected light does not carry any information about the patterns. Only scattered light carries the information about the patterns.

With continuing reference to FIG. 1A, the scattered light 116 passes through an off-axis region of imaging system 122 while the directly reflected light 114 passes through the central region (i.e., on-axis region) of the imaging system. Thus, the light reaching the first detector 180 has two different components, namely scattered light 116 and directly-reflected light 114. The directly reflected light is frequently called specularly reflected light or just specular light in the optics community. Therefore, the directly reflected light will also be called "specular component" and the scattered light will also be called "scattered component" herein. The scattered component will also be called "optical signal" or simply "signal" herein in the sense that it carries all the information about the object. The optical electromagnetic field will also be called "signal field" and this usually refers to the scattered component.

Not all the light 114 and 116 coming out of the sample 30 carries information. Usually, only a small portion of the light reaching the detector 180 carries useful information. We therefore distinguish between information-carrying light and non-information-carrying light. All the light coming out of the sample will not be called signal herein. Only information-carrying light will be called signal light or simply signal herein. In optical overlay measurement systems, overlay information is carried by the scattered light 116 only, more specifically the light scattered by targets T. The specular component 114 may carry some information about the films deposited on the wafer, but it does not carry any information about overlay. Signal light is the most important light component. However, it turns out that the non-signal light, i.e., the specular component 114, can also be very useful, because it can amplify weak signal light noiselessly. The notion of the specular component 114 serving as a noiseless optical amplifier is discussed below.

The specular component 114 passes through phase shifter 162 located at pupil plane 161 of the imaging system 122. The phase shifter 162 alters the relative phase between the specular component 114 and the scattered component 116. FIG. 1A shows only one phase shifter 162 for ease of illustration and discussion. However, in practice, the phase shifter 162 of system 100 can comprise a variable phase shifter or multiple fixed phase shifters supported by support member 164 in the form of a mechanical carriage that supports phase shifters having different amounts of phase shift. The phase shifter 162 serves two main purposes: the optical amplification of a weak overlay signal and the determination of the complex amplitude of the scattered component 116.

Also, many different kinds of phase shifters 162 can be effectively employed. The example system shown in FIG. 1A has a phase shifting plate 160 with one phase shifting coating 162 in the middle. It shifts the phase of the specular component by changing the optical path length of the specular component slightly. The amount of phase shift is simply $$\text{Phase shift in radian} = \frac{2\pi(n-1)t}{\lambda} \quad (2)$$

where
n=Refractive index of coating material
t=Thickness of the coating
λ=Wavelength The phase shifter depicted in FIG. 1A is a fixed phase shifter providing only one phase value. However, in order to cover all different kinds of targets and situations, multiple phase values need to be available. In order to provide multiple phase values, the phase shifter can be made with a variable phase shifting material such as liquid crystal or electro-optic material. Another way of providing multiple phase values is using multiple phase plates, each with a different phase shifter coating. A phase plate that provides an optimum amount of phase shift for any specific application can be chosen and then inserted into the imaging system using a mechanical loading system 164 such as turret, carousel, cassette, sliding stage, etc. The phase control needs to be performed in a precise fashion. Consequently, the whole phase control system in the disclosure is an elaborate high precision system composed of multiple high precision parts. The phase control system is one of the most important pieces of hardware in the disclosure. It will also be called a "phase controller" herein.

After passing through phase shifter 162, both the scattered component 116 and the specular component 114 pass through second beam splitter 170 and are received by detector 180. The detector 180 converts the detected light into electrical signals. The detector 180 (and the other detectors) can be any one of the commercially available image sensors, such as two-dimensional charge-coupled devices (CCDs), complementary metal-oxide-semiconductor (CMOS) image sensors, etc.

As stated previously, scattered light 116 from the sample 30 carries overlay information. To achieve high accuracy in the overlay measurement, the imaging system 122 needs to collect as much of the scattered light 116 as possible. In an example, imaging system 122 is diffraction-limited. On the other hand, the image processing methods disclosed herein in connection with making an overlay measurement can take into account aberrations present in system 122. Therefore, imaging system 122 can have aberrations and the methods disclosed herein can tolerate a much larger amount of aberrations than prior art optical overlay measurement systems. However, high-quality imaging of imaging system 122 is typically preferred.

When the numerical aperture is high and aberrations are low, the spatial resolution of the imaging system 122 at the object plane OP is much higher than the spatial resolution of detector 180. Consequently, to avoid losing information during image detection, in an example the magnification of the imaging system 122 is relatively high.

FIG. 1A shows system 100 as has having a relative a low magnification at the image plane IP for ease of illustration. In practice, system 100 can have very high magnification M, such as 100× or even greater. The numerical aperture (NA) of imaging system 122 can also be relatively high, e.g., 0.5 or greater.

The magnification M is usually larger than required by the Nyquist criterion to avoid information loss. The Nyquist magnification $M_N$ is an equivalent specification to the Nyquist sampling interval and is expressed as follows.

$$M_N = \frac{4 \times (NA) \times (\text{Detector pixel interval})}{\lambda} \quad (1)$$

Light source 110 can be any bright light source, such as a short arc lamp, super luminescence diode, laser, etc. In an example, light source 110 is configured to generate laser beam 112 having a single spatial mode to allow a clean separation between the scattered component 116 and specular component 114 at the pupil plane 161. It can be difficult to achieve good spatial uniformity over the whole field of view of imaging system 122 with a single spatial mode illumination beam 112. However, this is usually not a problem because the spatial non-uniformity is highly static and consequently can easily be calibrated out via image processing in controller 150.

Even if laser beam 112 with a single spatial mode is preferred, light source 110 does not need to generate single temporal mode. Actually, in most applications including overlay measurement, a large number of temporal modes are preferred because this can reduce the coherence length of the beam and consequently reduces or eliminates coherent interferences from stray light or ghost images.

In FIG. 1A, a phase shifting element 162 can be located in the path of the specular component, i.e., on axis A1. Thus, the phase of the specular component 114 is changed when the phase shifting element is changed, e.g., by replacing with another phase shifting element. However, the phase that matters is not the absolute phase but rather the relative phase between the scattered and specular components 116 and 114. Therefore, the phase shifting element 162 can be in the path of either the specular component 114 or in the path of the scattered component 116 (i.e., can be off-axis). However, a phase shifting element 116 in the path of the specular component makes for a simpler arrangement because the etendue of the specular component 114 is usually much smaller than that of scattered component 116. This makes fabrication of phase shifter 162 much easier.

The specular component 114 can also be attenuated to improve the contrast of the raw image captured by first detector 180. In an example, this is accomplished by adding a partially absorbing or reflecting film in the path of the specular component. In an extreme case, the specular component 114 can be completely blocked out. In this case, imaging system 122 is configured to operate in a dark-field mode. The dark-field mode is expected to be useful when the overlay signals, i.e., the scattered light component 116 from targets T, are strong. In this case, the signal amplification by the specular component 114 is not needed and can be blocked so that all of the light detected at first detector 180 is information-carrying light.

Removing the specular component 114 removes any interference between it and the scattered light 116, but there remains interference between the scattered light components originating from different points on the object, and this interference must be taken into account to achieve the overlay accuracy required. Thus in some situations, a very high signal-to-noise ratio can be achieved without the presence of the specular component 114. An important application of dark-field mode imaging is the overlay measurement in double- or multiple-patterning lithography. In double- or multiple-patterning lithography, all the targets T are in the top layer. No absorbing or opaque film covers the targets T. Consequently, strong overlay signals and a high signal-to-noise ratio can be obtained by blocking out the specular component.

Figure 1B:
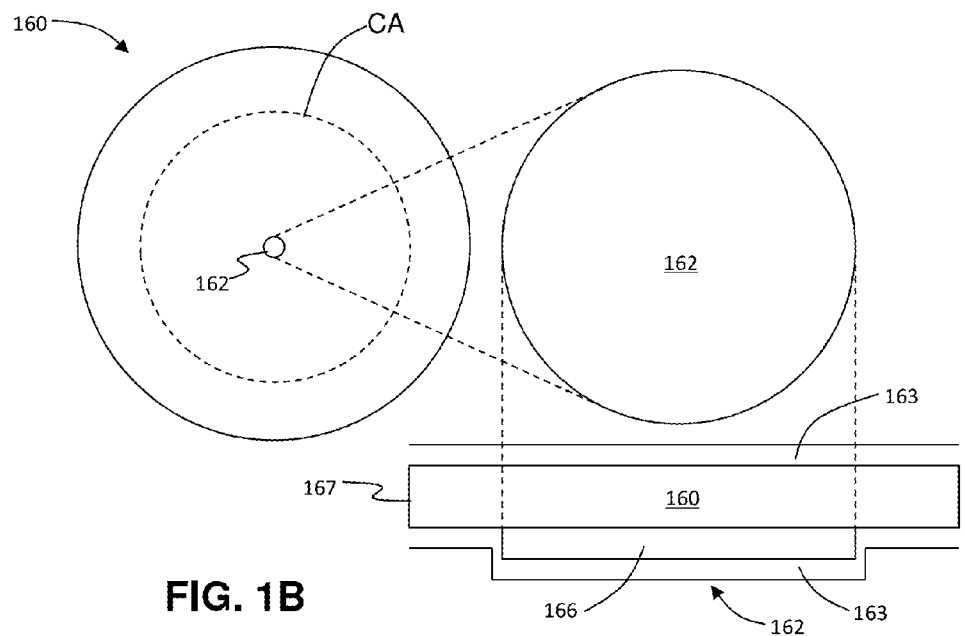
FIG. 1B shows an example phase control plate with a thin film phase shifter.
Figure 1C:
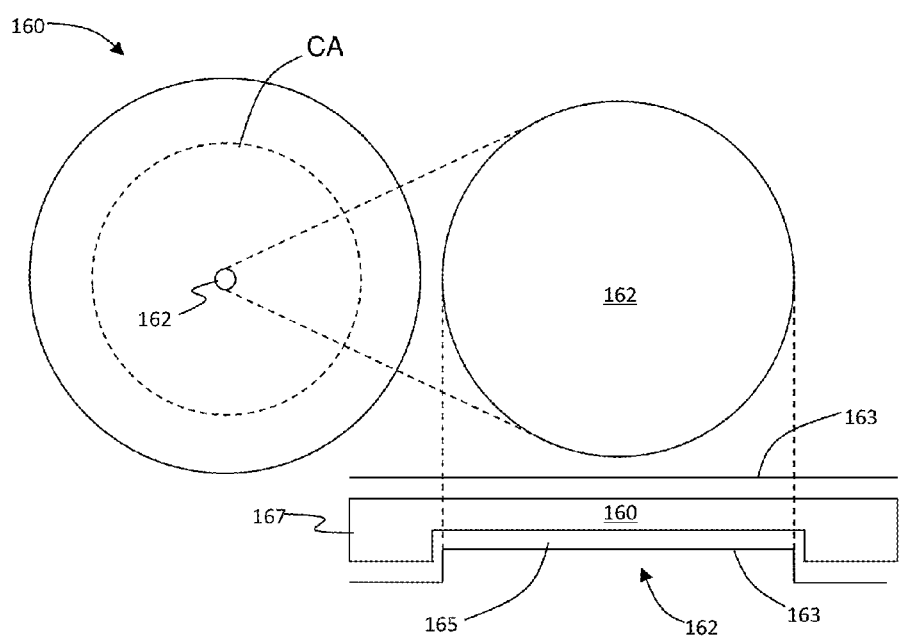
FIG. 1C shows an example phase control plate with a thin well phase shifter.

FIGS. 1B and 1C are close-up views of example phase shifting plates 160 that illustrate two different types of phase shifters 162. The clear aperture of the phase shifting plate 160 is denoted CA. One simple way of making a phase shifter is to apply a thin film coating 166, while another way is to etch a shallow well 165 on a glass substrate 167. The thickness (or depth) and lateral extent of the thin film (or well) are highly exaggerated in order to render them visible. The actual film thicknesses and well depths are only on the order of a wavelength. Their lateral extent is usually a few tens or hundreds microns. Antireflection coatings 163 can be added on the top and bottom surfaces of phase plate 160 to reduce stray light and ghost images.

Thus, thin film 166 or well 165 forms a tiny island or pit on a transparent glass plate 167. Thin films 166 or wells 165 can be formed into other shapes, such as a ring shape as in conventional phase contrast microscopes. This kind of shape allows US to use an extended light source such an arc lamp, halogen lamp, etc. However, this configuration has the disadvantage of introducing phase changes to some portion of the scattered component 116 of the collected light, thereby resulting in degradation in the image quality. Thus, the use of phase shifters 162 with substantial lateral extent is discouraged. In an example, laser beam 112 with a single spatial mode, along with phase shifters 162 made as small as the diffraction spot of the laser beam is employed in system 100.

Shallow wells 165 can be created by etching away a small amount of material from the substrate 167. Conceptually, a shallow well 165 can be considered as a thin film with negative thickness and similarly a thin film can be considered as a shallow well with negative depth. Therefore, the meanings of "thin film" and "shallow well" are broadened to include each other and the two expressions will be used in this broader sense from now on.

Thin-film phase shifters have several drawbacks. The most severe drawback is that they cannot shift the phase in a continuous fashion. Only discrete phase shifts are allowed. This discreteness in phase shifting can compromise the performance of system 100. Another drawback is that phase change requires a mechanical movement of the phase shifter plate 160. Mechanical movement is usually slower than other kinds of controls such as electro-optical control and hence can affect the speed or throughput of the system significantly. However, the thin film type phase shifter 162 has important advantages too. First, it is not sensitive to the polarization of light beam 112. That is, it allows any polarization to pass through without causing any significant change to the polarization. This is an important advantage because it allows for changing the polarization of the illumination light freely. The change of polarization of the illumination light may improve the image contrast for some types of targets T, such as those made with multiple fine lines.

Another important advantage of a thin film type phase shifter 162 is that it does not require any wiring to be placed in the optical path. The obscuration caused by wiring, which is usually unavoidable in the case of an electrically-controlled phase shifter, can distort the image of the target and impact the overlay measurement severely. Thus, the absence of wiring can be an important advantage of thin film type phase shifters.

The amount of phase shift introduced by a phase shifter 162 can be determined by taking images of one or more known patterns P placed at the object plane OP and processing them using an intelligent image processing method, such as a model-based regression method, which will be explained later. However, more direct methods are also available. They include physical measurement of film thickness, ellipsometric measurement of the film characteristics, etc. However, the most straightforward way of determining the amount of phase shift is to use a conventional phase-shifting interferometer, such as a Twyman-Green interferometer. This kind of measurement can achieve an accuracy of a few degrees routinely and much higher accuracy with more careful handling of the instrument.

As stated previously, other kinds of phase shifters, such as an electrically-controlled phase shifter can be employed for phase shifter 162. Suitable examples of electrically-controlled phase shifters are electro-optic and liquid crystal phase shifters. Many books and articles describe how to build electrically-controlled phase shifters. For example, the construction of an electro-optic phase shifter is well-described in the Handbook of Optics Volume II, Second Edition, McGraw-Hill, Inc, 1995, pp 13.15-13.18. The construction of a liquid crystal phase shifter is well-described in H. Kadono, M. Ogusu, S. Toyooka "Phase shifting common path interferometer using a liquid-crystal phase modulator" Optics Communications 110 (1994) pp 391-400. Electrically-controlled phase shifters are fast and do not require any moving parts. However, they are usually polarization sensitive and work as a pure phase shifter only for two specific polarization states called eigen polarizations. Refer to Kenneth F. Hulme "Oblique-Cut Longitudinal Electro-optic Modulators", IEEE Journal of Quantum Electronics, Vol. QE-7, No. 6, June 1971 for the discussion of polarization sensitivity of electro-optic phase shifters. Many other kinds of phase shifters are also available. The construction of other types of phase shifters is described in U.S. Pat. No. 7,986,412.

As discussed above, phase shifter 162 is preferably operably disposed at or substantially close to the pupil plane 161 or the aperture stop AS of the imaging system 122 in order to spatially separate the specular component 114 from the scattered component 116 in a clean fashion, and also to achieve uniform imaging performance over the whole imaging field. The primary pupil conjugate is the aperture stop of the imaging system 122. The phase shifter plate 160 is placed at or close to the aperture stop plane in the imaging system shown in FIG. 1A.

Lateral misalignment of the phase shifter 162 relative to the center of the specular component 114 can adversely affect the accuracy of overlay measurement. Therefore, the phase shifter 162 needs to be aligned accurately relative to the specular component 114. This kind of alignment can be done in several different ways. One way that does not require extra hardware is lateral scanning of the phase shifter plate 160 while observing the change of intensity distribution at the image plane IP using first detector 180. This measured intensity distribution will be very similar to the intensity distribution at the object plane OP when the center of the phase shifter 162 coincides with the center of the specular component 114. In this kind of alignment, the absolute positions of the specular component 114 and the phase shifter 162 at the pupil plane 161 are less important than their relative position. Therefore, we can choose either the phase shifter 162 or the illumination beam 112 for the positional adjustment.

However, this alignment method has a drawback that when the phase shifter 162 misses the specular component 114 completely, a time-consuming spiral search for the specular component may be required. This kind of drawback can be avoided if the pupil plane 161 is imaged onto second detector 182 using a pupil relay lens 172. The phase shifter 162 is located at the pupil plane 161. Therefore, the pupil relay lens 172 forms an image of the phase shifter 162 at the center of second detector 182. This allows for direct observation of the phase shifter position. The image formed at second detector 182 may not have much contrast when the amount of phase shift introduced by the phase shifter 162 is small. However, the image contrast can be enhanced significantly by processing the image electronically, e.g., in controller 150.

System 100 can tolerate much a larger focus error of the sample 30 as compared with prior art overlay measurement systems. However, a well-focused sample 30 is expected to enhance the system performance and to reduce image processing time. Thus, in an example, system 100 includes an autofocus system AF. In an example, autofocus system AF is configured as a through-the-lens system that includes first beam splitter 120, aperture plates 190 and 194, image separators 191 and 195, imaging lenses 192 and 196 and third and fourth detectors 184 and 186. The autofocus system AF takes two dark-field images of all the patterns P inside the field of view of the imaging system 122. The two images are formed by scattered light 116 passing through the two holes in the aperture plates 190 and 194. In order to separate the two images at the focus sensing image plane, respective image separators 191 and 195 are inserted in the optical path. The image separators can be made in many different ways. For example, they can be made with two 45° folding prisms, as shown in FIG. 1A. They can also be made with tilted glass plates, wedged glass plates, etc. The example autofocus system AF of FIG. 1A includes two detectors 184 and 186. However, these can be combined into a single large detector (image sensor), which is usually easier to calibrate. A focus error causes a linear change in the positions of the two images on their respective detectors 184 and 186 in opposite directions. Thus, the example autofocus system AF can tell not only the amount of focus error but also the sign or direction of the focus error.

The users of optical overlay measurement systems such as system 100 generally desire the following features:

1. In-die targets: As mentioned previously, the new trend is in-die targets to improve the correlation between the overlay error measured using overlay targets and that error actually found in the functional patterns. That is, overlay measurement targets need to be placed inside of, not outside of, dies in the future. There is very little room inside a die in which to print the existing targets. Therefore, in-die targets needs to be much smaller than the existing targets, which are generally printed in the scribelines. Thus, the new overlay measurement system should not require large targets. It should be able to work with very small targets. Ideally, a whole target should not take more than 5 µm×5 µm area. Existing optical overlay measurement systems either cannot work with small targets at all, or, at best, produce unacceptably poor measurement results with small targets.
2. Flexible target designs: The real estate available for in-die targets is not only extremely limited but also varies significantly in its shape. In order to fit targets inside the available real estate, most of the existing restrictions on target design should be alleviated or removed to provide flexibility. New targets should be allowed to have almost any size and shape. Accordingly, the new optical overlay measurement system should be able to handle targets having all kinds of different sizes and shapes. Existing optical overlay measurement systems can accept only very limited target designs and consequently put too many restrictions and conditions on target design.
3. Handling of asymmetric targets: Almost all the targets used for overlay measurement have three dimensional profiles. Ideally, the profile of an overlay target should be symmetric. However, in a lot of real cases, targets have some amount of asymmetry in their profiles. If the asymmetry is not treated accurately, it can cause a significant amount of error in the overlay measurement. None of the existing overlay measurement systems can handle an asymmetry in target profile properly.
4. No target capability: Sometimes, there can be no real estate available for targets. In this case, the only available patterns that can be used for overlay measurement are parts of the functional patterns. All the existing optical overlay measurement systems require specifically designed targets. They do not work without targets. They cannot use part of the functional patterns to measure overlay error.
5. Weak signal handling capability: In-die targets are expected to generate much weaker signals due to their small size. In addition, the popular use of opaque films which overlay the target can attenuate the overlay signal coming from any covered targets severely. The only means the existing optical overlay measurement systems provide to tackle this kind of problem is a change of wavelength. However, in many cases, changing the wavelength does not increase the signal strength enough. Frequently the measurement fails at all the available wavelengths. This is one of the main causes of poor measurement accuracy or measurement failure with existing overlay measurement systems.

6. Handling of low signal-to-noise ratio: Weak overlay signals can be overwhelmed easily by detection system noise. This results in a low signal-to-noise ratio. In order to avoid this problem, the weak overlay signal should be amplified in a clean fashion before detection. None of the existing optical overlay measurement systems provide any means to amplify the weak overlay signals in a clean fashion.
7. Filtering of focus error: The overlay measurement can be affected by the sample being out of focus. Therefore, the effect of focus error needs to be filtered out during image processing. Existing overlay measurement systems have no other means than maintaining accurate focus mechanically to avoid the detrimental effect of focus error. Maintaining focus is not only difficult, but also imperfect because the best focus position is not fixed mechanically, but depends on the structures of films and patterns on the sample in a complicated way. In existing optical overlay measurement systems it is impossible to isolate or filter out the focus error during overlay measurement.
8. Filtering of aberrations: Aberrations in the imaging system of the overlay measurement tool can affect the measurement result significantly. Especially, odd-order aberrations such as coma can distort the overlay error measurement tremendously. Therefore, aberrations need to be calibrated out during system calibration or filtered out during signal processing. Existing optical overlay measurement tools can neither calibrate nor filter out the aberrations. Therefore, the optical systems used in the existing overlay measurement systems need to be built almost perfectly. However, building an optical system with negligible aberrations is extremely difficult and costly. The level of perfection required for the optical systems used in the next generation overlay measurement tools is so high that it is impractical or too risky to pursue the existing development path.
9. Filtering of pattern interferences: Another critical issue is the interference from the surrounding patterns to the target. This is commonly called the proximity effect in semiconductor industry. This was not much a problem when the targets are large or the precision requirement on overlay measurement was relatively loose. However, currently, this is one of the main sources of overlay measurement error. One way of reducing the interference is to widen the clear area around the target. However, this requires an even larger area to be allocated to a target. This is not only going against the general trend of assigning less real estate to targets, but is also not acceptable in majority of applications. Therefore, next generation overlay measurement system needs to have a means to filter out the interference from the surrounding patterns. None of the existing overlay measurement systems can filter out this source of interference.
10. Handling of inter-target interference: As stated previously, an overlay target is actually made of a group of targets each of which originates from a different process layer. The individual targets in a whole target set are placed very closely to each other. The spatial closeness of individual targets can cause a large amount of interference between individual targets at the image plane. This can cause inaccuracy and also nonlinearity in overlay measurement. This is still less a problem than the interferences from surrounding patterns, thanks to the geometrical symmetries in current target designs. However, this can be another grave issue when some targets need to be asymmetrically designed due to the irregular shape of the space available for target printing.
11. Easy troubleshooting: A system with no trouble is possible in theory. However, in the real world, a complex system such as overlay measurement system can never be completely trouble free. Therefore, the real issue is not the occurrence of trouble, but how quickly the trouble can be resolved. In order to resolve a malfunction quickly, it is usually necessary to find the underlying cause of the trouble quickly. Existing systems are not amenable to a quick diagnosis, because they do not model the image faithfully. Without a faithful image model, it is very hard to find out what went wrong or where the source of the trouble is.

The inventor has determined that there are two main underlying issues that limit the accuracy of an overlay measurement: low signal strength and inadequate image modeling. The systems and methods herein address these two underlying issues to provide an improved accuracy of the overlay measurement.

A low overlay signal strength ("low signal") can be acceptable if the detector system is noiseless. The reason why low signal is not acceptable is that there is no noiseless detector system. This is especially true in industrial systems that include overlay measurement systems where signals need to be detected at high speed. It is well known that detector system noise increases rapidly with the increase of detection speed. Therefore, high detector system noise is unavoidable in industrial systems. High detector system noise swamps the weak signals resulting in a low signal-to-noise ratio. Even if the intrinsic signal-to-noise ratio, which is defined as the signal-to-noise ratio of the signal itself, is high, a low signal-to-noise ratio is not avoidable at the output end of the detector system. In order to overcome this problem and recover the original intrinsic signal-to-noise ratio, the weak signal must be amplified noiselessly before its detection.

It turns out that the specular component 114 that carries no information can be turned into a noiseless optical amplifier. That is, by interfering the low signal 116 with the specular component 114, the signal can be amplified in a noiseless fashion. This is called noiseless optical amplification and is explained in U.S. Pat. No. 7,986,412. However, the specular component 114 does not automatically become a noiseless amplifier. To turn the specular component 114 into a noiseless optical amplifier, the relative phase between the signal and the specular component should be close to 0° or 180°. This is why the imaging system 122 of the disclosure includes phase shifter 162. The phase relationship between the scattered and specular components 116 and 114 depends on structure of patterns P and consequently can be any value at sample 30. Therefore, without the phase shifter 162, the noiseless amplification cannot be guaranteed. Actually, a wrong phase relationship can make the specular component an extremely noisy amplifier. Therefore, phase control is an absolute necessity for consistent noiseless amplification of weak signals.

The use of phase control in system 100 and the method herein allow system 100 to reach the theoretical limit of signal-to-noise ratio. This means that even if other equivalently powerful techniques are possible, no systems and methods can be more powerful than those disclosed herein. This also means that if a weak signal problem cannot be solved with the phase control technique, it cannot be solved with other techniques either. In this case, the intrinsic signal-to-noise is too low. There can be no other solution than increasing the intrinsic signal-to-noise ratio. Methods that can increase the intrinsic signal-to-noise ratio include more intense illumination, a longer signal collection time, removing the opaque films that cover the target, etc.

There is another important feature the phase controller provides. If we take three or more images of the same sample with different phase values, we can determine the complex amplitude of the optical field at image plane IP. It is crucial to know the complex amplitude, not just the amplitude, of the optical field because it allows accurate modeling of the images. It is extremely difficult to model the image without knowing the complex amplitude. As stated previously, without generating an accurate image model, an accurate estimation of overlay error is impossible.

The systems and methods disclosed herein take a full advantage of the phase control system employed herein. It takes multiple images of the same sample with different phase values and determines the complex amplitude of the optical field at the image plane IP using an analytical regression method. Then, the complex amplitude values are used to generate the initial image model. The initial image model is refined by so called regressional image processing to produce an accurate image model. The accurate image model automatically yields the accurate overlay error values even in the presence of all the interfering patterns around the target. A more detailed explanation of the whole process is presented in following signal processing sections. Thus, the phase controller enables precision overlay measurement.

The systems and methods disclosed herein utilize an accurate or faithful model of the image. Accurate image modeling is not needed when targets T are large because the relationship between target image and overlay error is very simple. A geometrical image model is good enough. The overlay error is just the relative lateral shift between the images of different targets. An accurate estimation of overlay error can be obtained algebraically without establishing any accurate image model. This is basically the way the existing optical overlay measurement systems extract overlay information from target images. However, as target size shrink, the simple algebraic solution breaks down. The addition of ad hoc patches has helped extend the life of the algebraic solution, but as target sizes shrink further, even the ad hoc patches run out of steam.

The systems and methods disclosed herein do not try to improve the existing methods of overlay error extraction from target image but rather involve a completely different approach to the overlay problem. The new approach is a model-based approach that establishes an accurate image model to determine the overlay error accurately. The image modeling process is outlined in the flow diagrams shown in FIG. 3A. A large number of parameters are required to model the image accurately. Overlay error is just one of the parameters that are used to model the image. In order to determine the overlay error accurately, many other parameter values need to be determined at the same time using a regressional image processing technique, which will be explained later. This model-based approach is very different from the existing approaches such as an edge-slope-based or an intensity-gradient-based approach, which does not generate any image model. The model-based regressional image processing technique adopted herein requires more computing resources than the existing image processing techniques used to determine overlay errors. However, the new image processing method is necessary because even if the signal is strong, it is much harder to extract accurate overlay information from target images when the targets are much smaller than existing ones, and when the surrounding patterns interfere with the measurement.

The target image carries overlay information. Therefore, overlay error can be determined by processing the target image properly. However, the target image is not a function of overlay error only. It is also a function of many other parameters, such as pattern-related parameters, system-related parameters, process-related parameters, etc. Typical pattern-related parameters are the sizes, profiles, locations and complex reflectance of the target and surrounding patterns. Typical system-related parameters are the aberrations and distortion of the imaging system, the z-position error of the sample stage, pixel-to-pixel sensitivity variation of the image sensor, etc. Typical process-related parameters are the variation of complex reflectance of patterns and the background across the wafer, film stress, etc.

Note that reflectivity, which is defined as |complex reflectance|$^2$ cannot characterize the reflection property of target or patterns fully while complex reflectance does. Therefore, complex reflectance rather than reflectivity should be used to fully characterize the reflection property of target or patterns. Overlay error is just one parameter in the whole set of parameters that determines the image. The image is a complicated function of all the parameters. The parameters are intertwined in the image in complex ways. Even with all the complexities, an approximate estimation of overlay error can still be done without knowing the correct values of the extra parameters.

However, an accurate estimation of overlay error is a different story. Almost all the extra parameters affect the overlay error estimation more or less no matter what kind of image processing method is used for the estimation. Any error in the values of the extra parameters can degrade the accuracy in the overlay error estimation. Therefore, in order to be able to determine overlay error with high accuracy, the values of almost all the extra parameters need to be known very accurately.

Thus, accurate determination of parameter values is very important in the disclosure. It turns out that we cannot determine all the parameter values at the same time. Some parameter values need to be determined before the start of overlay error measurement and some other parameter values need to be determined during overlay measurement, more specifically during the regressional image-processing step.

The parameters that are determined before the start of overlay error measurement will be called fixed or static parameters because they will not be varied during overlay measurement. The parameters that are allowed to vary during the regressional image processing step in the overlay measurement will be called floated parameters herein. Various techniques and technologies that can be used to determine parameter values will be discussed first and then the details of the new image processing method will be presented afterwards.

Most system-related parameters are static and can be measured precisely using special tools. For example, aberrations in the imaging system can be measured accurately using a Fizeau or Twyman-Green interferometer. The image distortion can be determined precisely by analyzing the image of a precision grid pattern. Thus, the values of system-related parameters can be determined in a straightforward way. However, the values of pattern-related or process-related parameters cannot be measured directly. Consequently, it is not easy to determine their values precisely.

One way of determining the values of pattern-related or process-related parameters is to compute the complex amplitude of the optical field at the object plane using a rigorous electromagnetic computation tool such as finite-difference time-domain computation software. The values of the parameters can be determined using this method as long as accurate pattern and process data are available. However, this method has several critical drawbacks. First, it takes a long time or a large amount of computing resources to rigorously compute the electromagnetic field values over patterns. Second, it is hard to get accurate process data because most of the actual production processes cannot be controlled accurately and consequently vary over the sample. Third, it is difficult to verify the correctness of the pattern data. Any erroneous pattern data will corrupt almost all the computed parameter values.

There is a better way of determining all the pattern- or process-related parameter values. This is called the model-based regression method. The process flow of this method is outline in the flow diagram shown in FIG. 9. It contains a regressional computation engine whose internal process flow is depicted in the dotted box in FIG. 9. It is an iterative method. In this method, first, we reasonably assume the values of all the parameters and generate initial model images based on the assumed parameter values. Then, the model images are compared with measured images and the difference computed. If the difference is larger than an acceptable level, the parameter values are changed and images of the new model are generated.

The new model images are compared again with the measured images to see if the difference is tolerable or not. If the difference is within an acceptable level, we stop the process and output the parameter values. If the difference is larger than the acceptable level, we repeat the process until the difference becomes smaller than the acceptable level. This method requires a relatively large amount of computing resources because multiple iterations of image computation are usually required. However, this method allows the parameter values to be determined accurately, even if the images are very complicated functions of the parameters.

Regression is a fitting process that fits a model to a reference by varying the model parameter values iteratively. Therefore, regression is also called a fitting program. Regression fits a model to a reference by minimizing their difference. Therefore, it is also called a minimization process. Any minimization can be converted to a maximization process by defining the difference metric differently. Therefore, regression can also be called a maximization process. There is no real difference between minimization process and maximization process. So, there is no need to distinguish between the two processes. Both processes are just simply called optimization processes. Thus, regression is synonymous with fitting, minimization, maximization and optimization. These different names for regression will be used synonymously herein.

There are many different regression methods, which have their own pros and cons. Regression methods are well described in many books such as "Numerical Recipes in C", William H. Press, Saul A. Teukolsky, William T. Vettering and Brian P. Flannery, Cambridge University Press, 1992. However, some regression methods are better suited for the determination of the kind of parameter values we are interested in. For example, the Levenberg-Marquardt regression method is well suited for this kind of application. Levenberg-Marquardt regression is known to be robust and fits the model image to the reference image very quickly as long as the initial parameter values are reasonably close to the final values and the parameters that are allowed to vary during regression are mutually uncorrelated or independent. Most mutual correlations between parameters can be found easily by taking look at the function of each parameter in image modeling. Obscure mutual correlations can be found by computing the correlation matrix. When a group of parameters are mutually correlated, we have to fix the values of all the mutually correlated parameters except one to reasonable values and float only one parameter in the group.

Most of the efficient regressions, such as the Levenberg-Marquardt regression, work well only when the initial values of the floated parameters are reasonably close to the final values. Therefore, it is important to set the initial values of the floated parameters close to their final values. Unfortunately, there is no general way to do that. However, the disclosure provides a means that can help us to set the initial values of the parameters properly. This is based on the fact that thanks to the similarity of the image to the object, if we know the complex amplitude of the optical field at the image plane, we can set the initial value of most floated parameters close to their final values. That is, if we know the complex amplitude of optical field at image plane, it is much easier to assign good initial values to the parameters needed for image modeling.

Figure 2A:
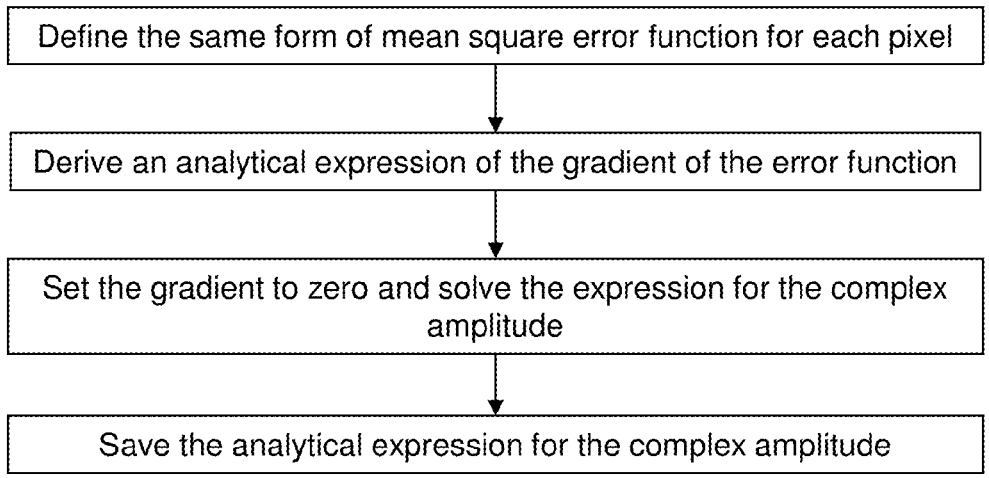
FIG. 2A shows the analytical regression procedure for the derivation of an analytical expression for the complex amplitude of optical field at each pixel of image sensor.

The systems and methods disclosed herein provide a way of determining the complex amplitude of the optical field at image plane IP. The method utilizes phase control using phase shifters 162. First, three or more images with different phase values are taken at the image plane IP by first detector 180. Then, the images are processed using analytical regression, which can produce an analytical expression for the complex amplitude values without requiring any initial values. The analytical regression process is set forth in the flow diagram shown in FIG. 2A and its mathematical details are presented below.

The intensity of the optical field at the image plane IP can be expressed as follows.)

$$I_n^{(0)} = |b\exp(i\theta_n) + s_x + is_y|^2 \qquad (3)$$

where
$I_n^{(0)}$ is the intensity distribution of the nth image
b is the amplitude of the specular component
$\theta_n$ is the phase value of the phase shifter
$s_x$ is the real part of the complex amplitude
$s_y$ is the imaginary part of the complex amplitude
Then,)

$$I_n^{(0)} = D + 2|b|(s_x \cos(\theta_n) + s_y \sin(\theta_n)) \qquad (4)$$

where $D \equiv |b|^2 + |s_x|^2 + |s_y|^2$: Specular term+dark field term  (5)

The error function is defined as follows in a least-square regression.

$$E = \sum_{n=0}^{N-1} (I_n - I_n^{(0)})^2 \qquad (6)$$

$$= \sum_{n=0}^{N-1} (I_n - D - 2|b|(s_x\cos(\theta_n) + s_y\sin(\theta_n)))^2 \qquad (6\text{-}1)$$

where N is the total number of images with different phase values and $I_n$ is the measured intensity distribution of the nth image We can treat D, $|b|s_x$ and $|b|s_y$ as independent fitting parameters and our goal is to find values for them that minimize the error function. The slopes of the error function with respect to D, $|b|s_x$ and $|b|s_y$ become zero at its minimum. Therefore, the solution satisfies the following three equations:

$$\frac{-1}{2}\frac{\partial E}{\partial D} = \sum_{n=0}^{N-1}(I_n - I_n^{(0)}) = 0 \qquad (7)$$

$$= \sum_{n=0}^{N-1} I_n - \sum_{n=0}^{N-1}[D + 2|b|(s_x\cos(\theta_n) + s_y\sin(\theta_n))]$$

$$= \sum_{n=0}^{N-1} I_n - ND - 2|b|\sum_{n=0}^{N-1}(s_x\cos(\theta_n) + s_y\sin(\theta_n))$$

$$\frac{-1}{4}\frac{\partial E}{\partial(|b|s_x)} = \sum_{n=0}^{N-1}\cos(\theta_n)(I_n - I_n^{(0)}) = 0 \qquad (8)$$

$$= \sum_{n=0}^{N-1} I_n\cos(\theta_n) - \sum_{n=0}^{N-1}[D\cos(\theta_n) + 2|b|(s_x\cos^2(\theta_n) + s_y\sin(\theta_n)\cos(\theta_n))]$$

$$= \sum_{n=0}^{N-1} I_n\cos(\theta_n) - D\sum_{n=0}^{N-1}\cos(\theta_n) - |b|s_x\left[N + \sum_{n=0}^{N-1}\cos(2\theta_n)\right] - |b|s_y\sum_{n=0}^{N-1}\sin(2\theta_n)$$

$$\frac{-1}{4}\frac{\partial E}{\partial(|b|s_y)} = \sum_{n=0}^{N-1}\sin(\theta_n)(I_n - I_n^{(0)}) = 0 \qquad (9)$$

$$= \sum_{n=0}^{N-1} I_n\sin(\theta_n) - \sum_{n=0}^{N-1}[D\sin(\theta_n) + 2|b|(s_x\sin(\theta_n)\cos(\theta_n) + s_y\sin^2(\theta_n))]$$

$$= \sum_{n=0}^{N-1} I_n\sin(\theta_n) - D\sum_{n=0}^{N-1}\sin(\theta_n) - |b|s_x\sum_{n=0}^{N-1}\sin(2\theta_n) - |b|s_y\left[N - \sum_{n=0}^{N-1}\cos(2\theta_n)\right]$$

Then, from equation (7):

$$D = \frac{1}{N}\sum_{n=0}^{N-1} I_n - \frac{2|b|}{N}\sum_{n=0}^{N-1}(s_x\cos(\theta_n) + s_y\sin(\theta_n)) \qquad (10)$$

By substituting equation (10) into equations (8) and (9):

$$\frac{-1}{4}\frac{\partial E}{\partial(|b|s_x)} = A - B|b|s_x - C|b|s_y = 0 \qquad (11)$$

$$\frac{-1}{4}\frac{\partial E}{\partial(|b|s_y)} = A' - C|b|s_x - B'|b|s_y = 0 \qquad (12)$$

where $$A \equiv \sum_{n=0}^{N-1} I_n\cos(\theta_n) - \frac{1}{N}\left(\sum_{n=0}^{N-1} I_n\right)\left(\sum_{n=0}^{N-1}\cos(\theta_n)\right)$$

$$B \equiv N + \sum_{n=0}^{N-1}\cos(2\theta_n) - \frac{2}{N}\left(\sum_{n=0}^{N-1}\cos(\theta_n)\right)^2$$

$$C \equiv \sum_{n=0}^{N-1}\sin(2\theta_n) - \frac{2}{N}\left(\sum_{n=0}^{N-1}\cos(\theta_n)\right)\left(\sum_{n=0}^{N-1}\sin(\theta_n)\right)$$

$$A' \equiv \sum_{n=0}^{N-1} I_n\sin(\theta_n) - \frac{1}{N}\left(\sum_{n=0}^{N-1} I_n\right)\left(\sum_{n=0}^{N-1}\sin(\theta_n)\right)$$

$$B' \equiv N - \sum_{n=0}^{N-1}\cos(2\theta_n) - \frac{2}{N}\left(\sum_{n=0}^{N-1}\sin(\theta_n)\right)^2$$

From equations (11) and (12):

$$|b|s_x = \frac{AB' - A'C}{BB' - C^2} \qquad (13)$$

-continued $$|b|s_y = \frac{A'B - AC}{BB' - C^2} \qquad (14)$$

Equations (13) and (14) are the general best solutions for the complex amplitude of the signal field. By substituting equations (13) and (14) into equation (10), $$D = \frac{1}{N}\sum_{n=0}^{N-1} I_n - \qquad (15)$$

$$\frac{2}{N}\left[\left(\frac{AB' - A'C}{BB' - C^2}\right)\left(\sum_{n=0}^{N-1}\cos(\theta_n)\right) + \left(\frac{A'B - AC}{BB' - C^2}\right)\left(\sum_{n=0}^{N-1}\sin(\theta_n)\right)\right]$$

The error function defined in equation (6) assigns the same weight to each image term. However, different weights can be assigned to different image terms in order to make the results more accurate. For example, it is a good idea to assign larger weights to the terms with low noise measured images and smaller weights to the terms with noisy measured images. The formulation of all equations with different weights to different image terms is a straightforward extension of the equations shown above.

Figure 2B:
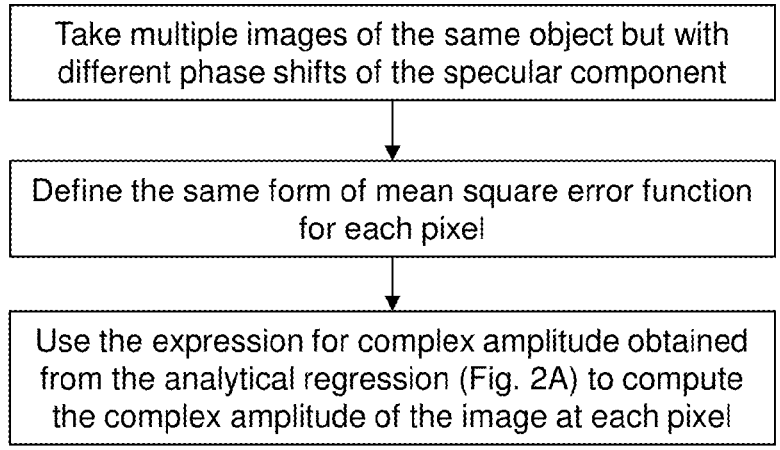
FIG. 2B shows the procedure for determining the complex amplitude at the image plane from multiple images of the same object but with a different phase shift of the specular component for each of the multiple images. The procedure uses the analytical expression of complex amplitude obtained from the analytical regression procedure shown in FIG. 2A.

The complex amplitude determination process is set forth in the flow diagram of FIG. 2B and uses the final results, equations (13) and (14), of the analytical regression. The pattern or process-related parameters are defined at the sample plane, not at the image plane. Therefore, the complex amplitude data at the image plane IP is not sufficient to determine the parameter values accurately. However, the initial values of the parameters do not need to be accurate. Approximate values are very acceptable. The complex amplitude data at the image plane IP is usually sufficient to determine the parameter values approximately.

When all the system-related parameter values are determined accurately and all the pattern-related parameter values are set to their initial values, we are ready to run a regression process, referred to herein as "model-based regressional image processing," to determine the pattern-related parameter values accurately. The process steps are set forth in the flow diagrams of FIGS. 3A, 3B and FIG. 9, which are explained in greater detail below in connection in the overlay determination process.

In order to run the regression, we need to establish the initial model images first. Because all the parameter values are determined at least approximately now, we can establish the initial model images using an imaging theory, such as Fourier optics. Then, we run the regression part of the process with the initial parameter values and initial model images. The regression program automatically varies the parameter values and model images until the model images fit the measured images well enough.

If the regression proceeded well and the difference between model images and the measured images are less than a specified level, we accept the final parameter values as the true parameter values. This is how the method is used to determine the pattern-related parameter values. This is also how the overlay error is determined. The only major difference between the determination of pattern-related parameters and the determination of overlay error is that the former usually uses multiple images of the same patterns with different phase shifts and the latter usually uses a single image taken with an optimum choice of phase shift. This method is more complicated than the methods used in existing systems. However, it is very flexible and can deliver much more accurate results, because it employs accurate image models.

When all the values of system-related parameters and pattern-related parameters are obtained, the overlay error determination process can be carried out. The overlay error determination process uses the same regression method as for the determination of pattern-related parameter values. The process is called model-based regressional image processing and is illustrated in the flow diagrams of FIGS. 3A, 3B and 9. In the regression process, overlay error is just one of the parameters that are varied iteratively for the generation of an accurate model image.

In order to minimize the regression time, we can vary the overlay error parameters only during the regression with all other parameters fixed to their initial values. However, this strategy can cause severe inaccuracy in overlay error results due to the unavoidable interferences of inaccurate parameter values with the overlay parameters. Therefore, an aspect of the method does not vary overlay error parameters only during the regression. During the regression, not only the overlay error parameters but also other non-static parameters such as the process-related parameters, illumination intensity, focus parameter, wafer position parameters, etc., are varied at the same time. This is useful because by assigning accurate values to all the static parameters and varying all the non-static parameters together with the overlay error parameters during the regression, we can eliminate all the interferences from the other parameters with the overlay error parameters and get accurate overlay results even if the surrounding patterns interfere severely with the overlay targets at the image plane.

Elimination of detrimental effects, such as the interaction between the parameters describing the overlay targets and the parameters describing the surrounding patterns, focus parameter, etc., can be considered as a kind of filtering. Therefore, this kind of elimination of detrimental effects is referred to herein as "regression filtering." The use of regression filtering for the elimination or at least significant reduction of inter-pattern interferences is one of the key features of the disclosure Regression filtering is a very powerful technique. However, it works properly only when the model image represents the actual image with sufficient accuracy. If the model image cannot represent the actual image accurately, the regression filtering can produce even less accurate overlay results than the existing image processing methods. Accurate modeling of the image is thus required to obtain the best (i.e., most accurate) overlay measurement results.

Detectors detect the intensity of the optical field incident thereon. Therefore, it is tempting to model images using the intensity of optical field. However, this cannot be done because the important mechanisms responsible for forming features in the image such as the diffraction by aperture stop, the interferences between patterns, aberrations, etc, cannot be modeled properly using only the intensity of the optical field. In order to avoid these problems in image modeling, the systems and methods disclosed herein uses the complex amplitude, or equivalently, both the amplitude and phase of the optical field to model images accurately. An optical field can be specified completely with the complex amplitude along with its polarization. Therefore, the use of complex amplitude rather than intensity allows us to model images with unprecedented accuracy and thus obtain highly accurate overlay measurements.

As explained above, the regression method used herein to get an accurate image model requires starting with approximate complex amplitude values at the object plane OP. This, in turn, requires US to know the complex amplitude values at the image plane at least approximately. However, the complex amplitude cannot be detected directly by an image sensor. This is a serious problem in conventional imaging systems, which cannot change the relative phase between scattered and specular components. However, system 100 is configured to change the relative phase between the scattered and specular components 116 and 114. System 100 can be used to determine the complex amplitudes of the optical field at image plane IP indirectly by capturing multiple images with different relative phase values and processing them in controller 150 using the analytical regression equations set forth above. Therefore, the difficulty of directly detecting the complex amplitude of the optical fields of the captured images is avoided by using indirect detection in system 100.

Image modeling starts from surface of sample 130, goes through imaging system 122 and ends up at the image plane IP. In this process, the first hurdle is the coarse sampling of the optical field at the object plane OP where sample 130 resides. The majority of patterns P on a semiconductor wafer are sharply defined. They usually carry sharply defined edges and corners. In image modeling, patterns on the sample surface are represented by their complex reflectance or the complex amplitude of the optical field at the sample surface. The complex amplitude of the optical field at the sample surface is an exact copy of the complex reflectance of the patterns P. The only difference between the two is the scaling factor determined by the intensity of the illumination light.

Consequently, the complex amplitude of the optical field at the sample surface also carries sharp edges and corners. Note that, in order to avoid unnecessary verbosity, the two terms, complex reflectance and complex amplitude of optical field at the sample surface, will be used in a synonymous fashion herein. In order to represent the complex amplitude or reflectance accurately, the optical field must be sampled in an extremely fine fashion. Otherwise, severe aliasing can happen at the image plane IP. That is, the sampling interval of the optical field must be extremely small. This causes two problems. Firstly, an extremely large amount of memory is required to store the sampled field data. And secondly, the time taken to process the sampled data is too long. Therefore, while it can be done, it is not practical to represent patterns P at the object plane OP even though the pattern representation at the sample plane can be understood most intuitively.

In order to avoid these problems, in an example embodiment patterns P are represented at the spatial frequency domain even though the pattern parameters are defined at the sample (object) plane in spatial coordinates. This is one of the key software features in the disclosure. The spatial frequency domain is at the pupil plane 161 in the imaging system 122. Therefore, the terms "spatial frequency domain" and the "pupil plane" will be used synonymously herein.

There are two pupil planes in imaging system 122, namely the entrance pupil plane and the exit pupil plane. The entrance pupil plane is the spatial frequency domain of the object or sample patterns P and the exit pupil plane is the spatial frequency domain of the image. Object and image planes are also called fields in optical parlance. The object plane OP is called the object field and the image plane is called the image field. Thus, the pupil is the frequency domain of the field.

Because the specular component 114, which represents a zero spatial frequency component, occupies a very small area in the middle of the pupil, the amplitude of any non-zero spatial frequency in the object plane OP is represented by a corresponding amplitude in the pupil plane 161 located at a radius from the center of the pupil where the radius is proportional to the frequency. The relationship between the complex amplitude representation at the object field and the representation at the entrance pupil is a Fourier transform of each other. The sharp edges and corners in the object patterns contain a broad range of spatial frequency components and consequently diffract the illumination light into a wide area in the plane containing the pupil. The finite size of the aperture stop AS that defines the edges of the pupil sharply limits the maximum frequency that can pass through the pupil to form the image. Consequently, neither extremely fine sampling nor sampling over an extremely wide pupil area is needed to represent the sharp features of the patterns P in the sample. Therefore, coarse sampling at the pupil plane is very acceptable as long as the sampling interval is smaller than Nyquist sampling interval. Also, the total number of samples required to faithfully represent the amplitude distribution in the pupil plane 161 is quite moderate because the pupil is bounded by aperture stop AS. This is the main reason why in one aspect of the disclosure, patterns P are represented at the pupil plane 161 rather than at the object plane OP.

The representation of patterns P at the pupil plane 161 allows all the sharp features in the patterns to be accurately modeled because they produce a broad spectrum of frequencies spread across the pupil plane. However, large, smooth pattern features, such as a slow variation of pattern reflectivity or profile across the field, are difficult to model accurately. This is because the spatial frequency component that represents large smooth pattern features is concentrated into a small area in the pupil plane and consequently quite fine sampling is required to represent the highly localized complex amplitude of the light. This is not an issue in the overlay measurement systems and methods disclosed herein because large smooth features in the patterns P do not carry much of the overlay-related information. Almost all overlay-related information is carried by small, narrow or sharp features in the patterns P, all of which can be represented accurately at the pupil plane 161, even with coarse sampling.

The pupil plane representation of patterns P requires that we derive the pattern representation analytically rather than numerically. As stated previously, the pupil plane representation of patterns P is the Fourier transform of the sample (object) plane representation. If we have a good sample plane representation, we can get the pupil plane representation by performing numerical Fourier transform such as fast Fourier transform of the sample plane representation. However, as explained previously, usually we cannot obtain a good representation of the patterns P at the sample plane, which makes numerical derivation of a pupil plane representation of the sample patterns impossible.

Instead we have to rely on analytical derivation, i.e., an analytical Fourier transform. The problem with analytical Fourier transform is that only very small number of functions can be analytically Fourier transformed. This means that only very special patterns P can have faithful pupil representation. However, the actual patterns P can have a large number of different shapes and an exact representation of the patterns P at the pupil plane is usually not plausible.

Fortunately, two facts allow us to resolve this issue. First, the Fourier transform is a linear operation that allows us to use the principle of linear superposition for the generation of pupil plane representation of any shape of pattern P. This means, if a pattern P cannot be Fourier transformed analytically, it can decomposed into multiple simple linearly superimposable subpatterns p1, p2, . . . that can be Fourier transformed analytically. Then, the Fourier transform of the original pattern P can be obtained by Fourier transforming every individual subpattern p1, p2, p3, . . . separately and summing the results.

A very useful simple subpattern is the box-function which is defined as:

$$\text{Box}(x, y) = \begin{cases} h & \text{for } \left|\frac{x}{w_x}\right| \le 0.5 \text{ and } \left|\frac{y}{w_y}\right| \le 0.5 \\ 0 & \text{else} \end{cases} \quad (15)$$

where h is height of the box function, $w_x$ is width of the box function in x-direction and $w_y$ is width of the box function in y-direction A box-function of any size, any height and any orientation can be Fourier transformed analytically. Any pattern P can be decomposed into a collection of box-functions of various sizes and heights and placed at various places. Therefore, in principle, any pattern P can be represented at the pupil plane 161 with the use of the principle of linear superposition. This is the way the disclosure obtains the pupil plane representation of any patterns on the object plane.

The accuracy of the representation obtained in this way cannot be perfect for most patterns in the real world. However, the accuracy of representation can be increased indefinitely by decomposing the pattern into finer and finer subpatterns. This is called asymptotic convergence of the pattern representation.

Another important advantage of pupil plane representation is that it is a straightforward matter to introduce different focus positions to each subpattern. This is because defocusing is just a multiplication of a complex function with unit magnitude that represents the defocus at pupil plane. It does not involve any complicated or time-consuming process such as convolution, Fourier transform, etc. This means that the pattern models in the disclosure can depict 3-dimensional profiles of targets and patterns accurately. This also means that the vertical separation between different targets or patterns can be modeled accurately in the disclosure.

One of the issues with the asymptotic convergence of a pupil plane representation is that some complicated patterns can require an enormous number of subpatterns in order to be represented at the pupil plane accurately. This can create undue computational burden requiring either a long processing time or a large amount of computational resources. However, it turns out this kind of problem does not arise in real systems thanks to the fact that most of the inaccuracy in the representation happens in the high-spatial-frequency parts, and the imaging system 122 filters out all the spatial frequency components higher than the cutoff frequency defined by the aperture stop AS.

In the case of typical targets T with surrounding patterns P, most of the inaccuracies in the representation happen in the extremely high spatial frequency regions, such as evanescent or non-radiant portions of the spatial frequency spectrum. Because imaging system 122 operates as a type of low-pass filter, patterns P need to be represented accurately only over the low-spatial-frequency region transmitted by the imaging system. The representation does not need to be accurate in the higher spatial frequency regions beyond the cutoff frequency of the imaging system.

Figure 3A:
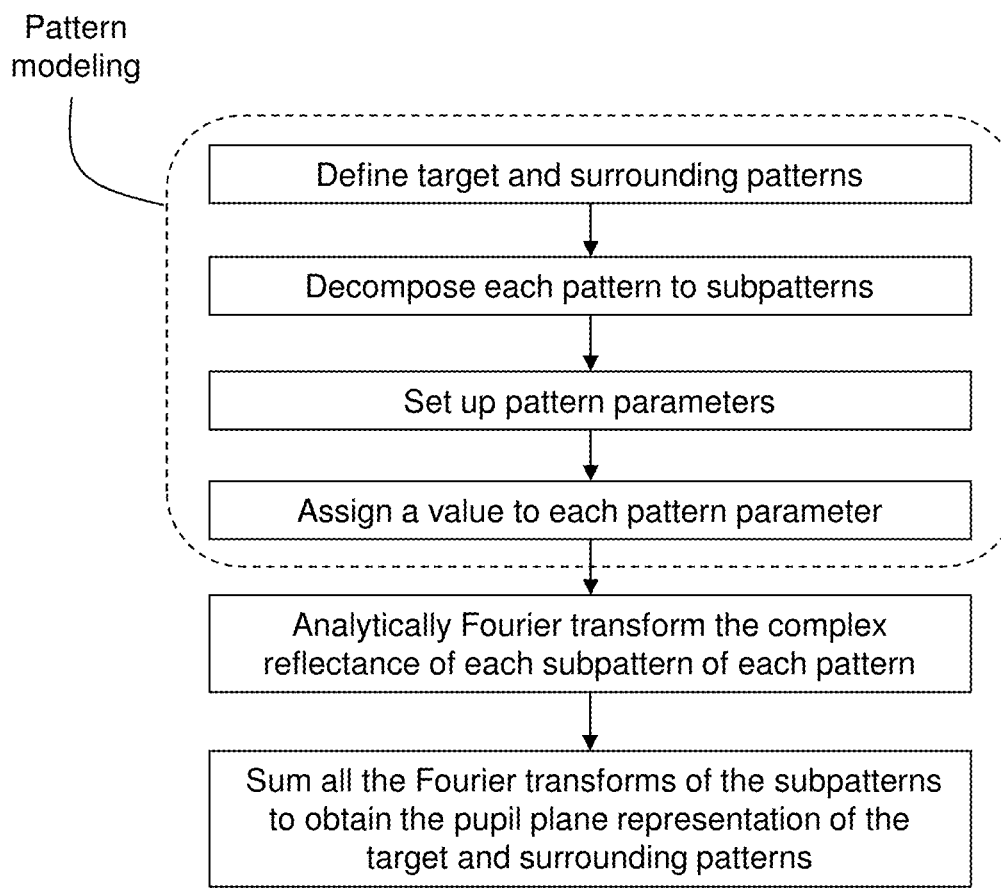
FIG. 3A shows the procedure for representing the patterns within the field of view at the entrance pupil.
Figure 3B:
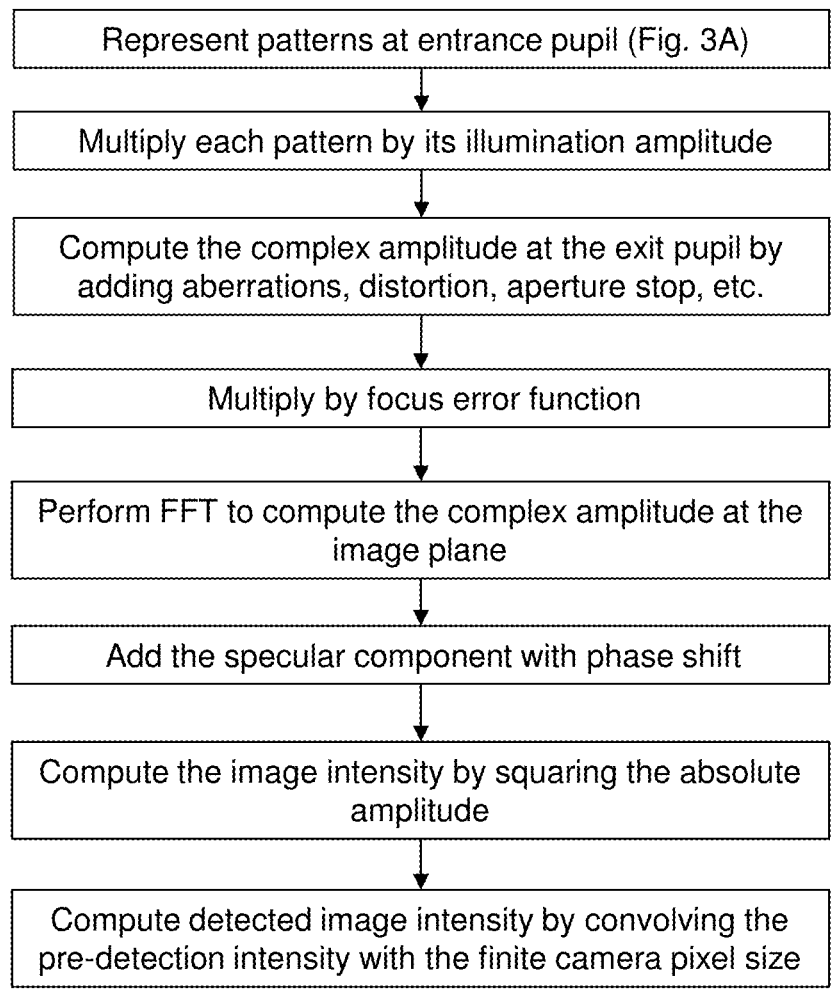
FIG. 3B shows the procedure for image modeling.

An accurate representation within the transmission band of the imaging system 122 does not require an extremely fine decomposition of the pattern P. Thus, an accurate representation of even complex patterns P can be achieved without using an extremely large number of subpatterns p=p1, p2, . . . . Also, subpatterns p are more flexible than actual patterns P because they are just a mathematical tool that supports linear superposition and consequently can overlap with each other without causing mutual interference. This kind of flexibility of the subpatterns p can be utilized to further reduce the number of subpatterns required. Thus, the systems and methods disclosed herein can represent any pattern P accurately at the pupil plane 161 using a reasonable number of subpatterns p. The pupil plane representation of all the patterns P can be carried out in software in controller 150. FIG. 3A sets forth the general procedure for the frequency domain representation of patterns P on sample 130.

In order to get an accurate overlay result, all the pattern-related parameters need to be known before image processing begins or determined during the image processing step. System parameters, such as aberrations, distortions, etc., must be accounted for in the image modeling. The aberrations and distortions can be included easily in the image modeling process thanks to the fact that the image model uses complex amplitude rather than the intensity of the optical field, and all patterns P are represented at the pupil plane 161. Aberrations are the departure of the wavefront of imaging system 122 from its ideal shape at the pupil plane 161, and can be represented as a complex function with unit magnitude at the pupil plane. The complex function that represents aberrations is called the aberration function. It is impossible to include aberrations in the image model if the model is based on the intensity rather than the complex amplitude of the optical field.

Thanks to the complex-amplitude-based image modeling employed in the systems and methods disclosed herein, it is very easy and straightforward to fully include the aberrations in the image modeling. Aberrations can be fully accounted for in the disclosure by simply multiplying the pupil plane representation of patterns P with the aberration function. This represents a significant advantage of the systems and methods disclosed herein as compared with all the existing overlay measurement systems that rely on the intensity of the optical field for the overlay measurement.

The only requirement for this simple aberration inclusion process is that the imaging system 122 must be substantially stationary or substantially shift-invariant in the image quality across the field of view. This condition is known in the art of optical design as the Abbe sine condition. This is a basic condition that all high-quality imaging systems must meet.

Adding distortion to the image model is straightforward because patterns P are represented at the pupil plane with a complex amplitude. Distortion is a small amount of lateral shift of patterns P away from their ideal positions at the image plane IP. This shift can be measured in many different ways. For example, a precision grid pattern can be imaged and the position of each grid line intersection in the image can be measured to determine the distortion. As explained previously, a small amount of lateral shift in a pattern P cannot be represented accurately at the object plane OP due to the finite sampling interval. However, the shift can be represented with extreme accuracy at the pupil plane 161 because the representation is simply a phase slope across the whole pupil. Thus, the systems and methods disclosed herein include the option of incorporating distortions in the images accurately by including them in the image model.

The aperture stop AS and the transmission variation across the pupil 161 can be treated similarly to an aberration. The difference is that the aperture stop AS and the transmission variation can be expressed with real functions. The two functions can be combined into a single function. Most aperture stops AS have sharp edges, which carry very high spatial frequency components. However, the FFT (Fast Fourier Transform) process that can be used to compute the complex amplitude of the model image has a limited spatial frequency bandwidth. The higher spatial frequency components beyond the bandwidth of the FFT process can create aliasing in the model images. However, in high NA imaging systems, the magnitude of the high spatial frequency components of the aperture stop is much smaller than that of the low spatial frequency components. Consequently, the aliasing can be negligible.

The optical field passes through the phase shifter 162. Not only the specular light 114 but also some low frequency non-specular components 116 can pass through the phase shifter 162. Therefore, the phase shifter needs to be modeled properly. Otherwise, measurable errors in the image model can arise. Even if the phase shifter 162 looks similar to an aperture stop AS with a constant phase value over the whole phase shifter coating, care needs to be taken to model it correctly.

The main difference between the phase shifter 162 and the aperture stop AS is their relative sizes. The phase shifter 162 is much smaller than the aperture stop. Consequently, it can have relatively strong high spatial frequency components compared with its low frequency components. A significant part of the high spatial frequency components can be outside of the spatial frequency bandwidth of FFT and consequently can cause aliasing in the image. Aliasing is the conversion of part of the high spatial frequency components into low spatial frequency components due to the limited bandwidth of the FFT process. This is an artifact of the FFT process and one of the primary sources of error in image modeling. Therefore, it is important to filter out all the high spatial frequency components located outside of the pass band of the FFT process.

In order to filter out the detrimental high spatial frequency components, first the phase shifter pattern needs to be Fourier transformed analytically and then sampled discretely. Then, the detrimental high frequency components in the sampled Fourier transform data are filtered out. Finally, the filtered data is inverse FFTed to get the intended model of the phase shifter 162. The phase shifter model obtained this way can now be multiplied with the pupil plane representation of the sample patterns in addition to the aberration function and the pupil transmission function. This completes the inclusion of a correct phase shifter model in the image modeling. Aberrations, aperture stop, pupil transmission and the phase shifter are static or fixed. Therefore, they can be combined into one complex static function called complex pupil transmission function to reduce the computing time.

Another important factor that needs to be included in the image model is defocus of the sample 130. This is important because sample defocus can affect the overlay measurement results significantly, but it is hard to maintain a perfect focus for the sample. In many cases, even maintaining a perfect sample focus using a closed-loop autofocus system is not sufficient, because of the slight difference between the two focal positions, one measured by the autofocus system and the other defined by the position yielding the highest image contrast. Thus, sample focus can be measured and controlled only approximately. This is one of the serious issues in prior art overlay measurement systems.

The systems and methods disclosed herein avoid this problem because the images are modeled using the complex amplitude of the optical field rather than just the intensity of the optical field. This allows the focus error to be treated as just another aberration and consequently treated the same way as the other static aberrations in imaging system 122. The only difference is that the parameters for static aberrations are fixed but the focus parameter remains floating during the regressional image processing. This approach to treating focus error eliminates the detrimental effect of focus error on overlay measurement quite completely. In other words, the regressional image processing filters out all the detrimental effects of focus error. It is another example of the filtering power of the model-based regressional image processing methods employed herein. The capture range of focus error of the regressional image processing method is usually larger than the focus error range of even poorly designed focus maintenance systems. Consequently, the systems and methods disclosed herein tolerate practically unlimited focus errors in most overlay measurement applications.

The physical entity that first detector 180 detects is the intensity of the optical field. Therefore, the image model should provide accurate intensity values of the optical field at the image plane IP. However, in order to get accurate intensity values, we have to know the accurate values of the complex amplitude of the optical field at the image plane first. This requires knowing the complex amplitude values of the optical field at the exit pupil.

In general, the transition from entrance pupil to exit pupil is a complicated process. However, in case of shift-invariant optical systems, which include the imaging system 122 of system 100, the process is straightforward. The complex-amplitude-based image modeling adopted by the disclosure allows us to get accurate complex amplitude values of the optical field at the exit pupil easily. As shown already, the complex amplitude of the optical field at the exit pupil is obtained by multiplying the complex amplitude representation of sample patterns P at the entrance pupil with the complex pupil transmission function and the defocus function. The complex amplitude computed this way represents reality accurately because it accounts for all the aberrations and all other system-related parameters. Thus, no guesses or assumptions are needed regarding the complex amplitude of the optical field in the disclosure.

The complex amplitude of the optical field at the image plane IP can be computed by simply Fourier transforming the complex amplitude at exit pupil. This can be done efficiently using a FFT program. The image intensity can be obtained by just squaring the absolute values of the complex amplitude of the optical field at the image plane IP. The detected image intensity values can be slightly different from the intensity values before detection because of the finite pixel size of detector 180. Therefore, in order to get accurate detected intensity values, we have to account for the finite pixel size of the individual pixels (detector elements) in detector 180. This can be done easily using the systems and methods disclosed herein because the detected intensity values are the convolution of the before-detection intensity with the finite pixel. This kind of convolution can be done efficiently by performing a FFT-based convolution rather than a direct convolution. In FFT-based convolution, both the before-detection intensity and the finite pixel are Fourier transformed and then the two are multiplied and finally the resultant is inverse Fourier transformed to get the detected image intensity, as noted in the flow diagram of FIG. 3B The effect from finite pixels is accounted for by convolving the before-detection model image intensity with the finite pixel in FIG. 3B. However, it can also be accounted for by deconvolving the measured image with the finite pixel. If a measured image is deconvoluted with the finite pixel, it becomes the intensity of measured image just before detection. Then, the before-detection measured images can be compared with the before-detection model images in the image processing procedures rather than comparing after-detection images. Deconvolution process is generally less stable than convolution process. However, it can save a sizable amount of time in regressional image processing because it allows avoiding a large number of repeated executions of convolution during the regressional image processing.

Figure 4A:
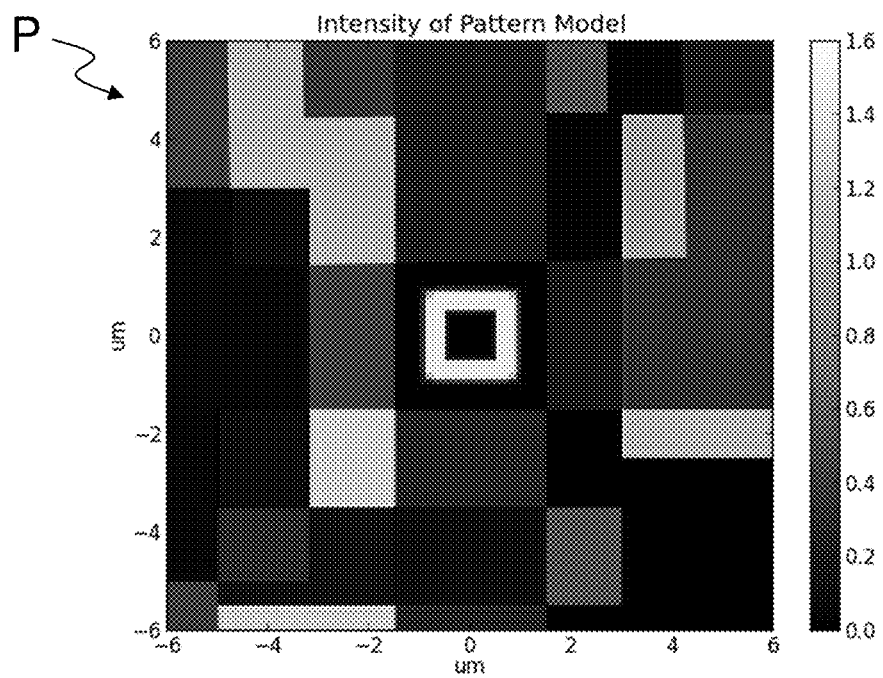
FIG. 4A shows the intensity of an example pattern model at the sample (object) plane.

FIG. 4A shows the intensity distribution of a synthetic pattern P whose image will be modeled. The actual size of the whole pattern is larger than 12 μm×12 μm. Only the central part of the whole pattern P is shown in FIG. 4A in order to show the target pattern more clearly. The pattern P has a small box-in-box type target at the center to represent an in-die overlay target design.

Knowing the intensity distribution of a pattern P is sufficient to generate a geometrical image model. However, as stated previously, specifying intensity or the reflectivity distribution alone is not sufficient to generate an accurate image model. We need to specify the complex amplitude or the complex reflectance of the whole pattern P. Thus, the complex amplitude or reflectance of the patterns is specified herein.

Figure 4B:
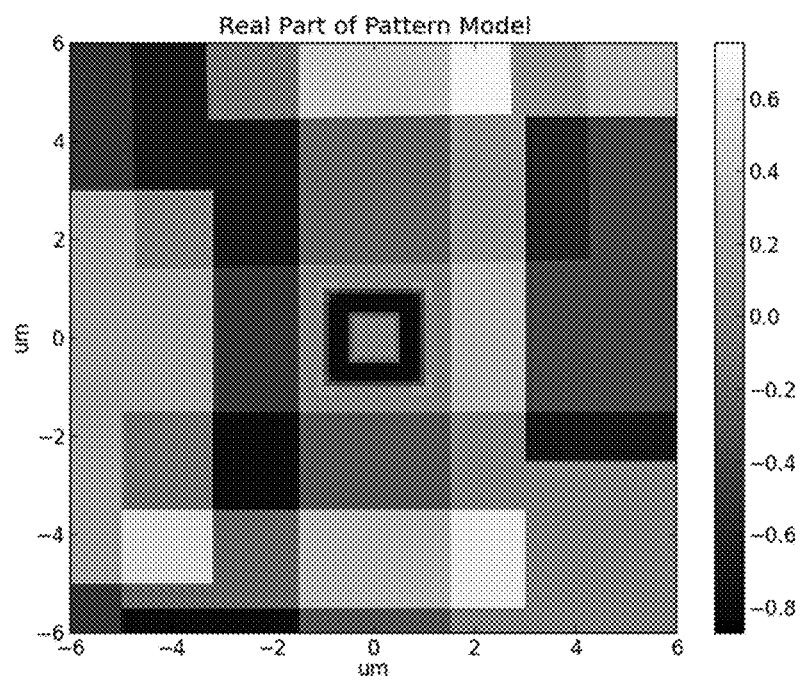
FIG. 4B shows the real part of the example pattern model at the sample plane.
Figure 4C:
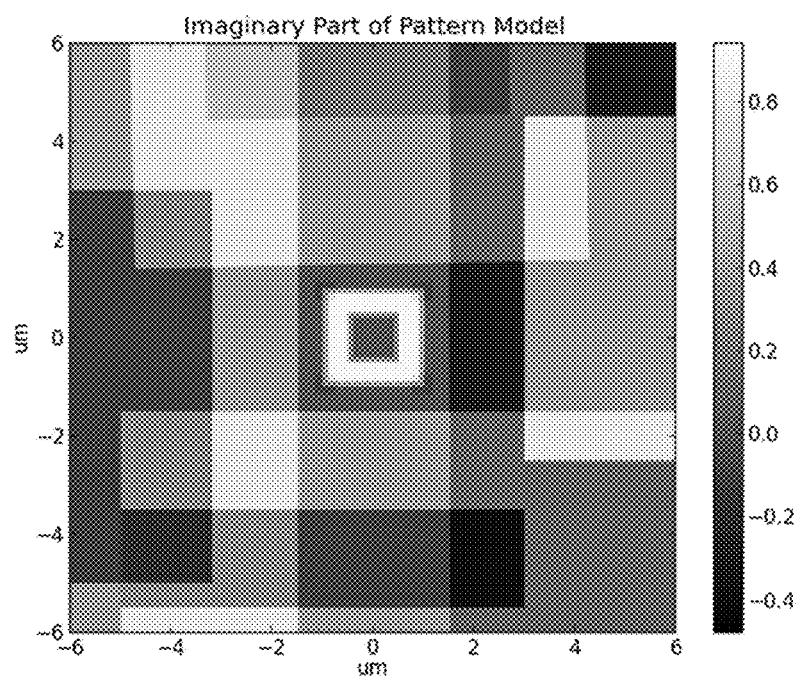
FIG. 4C shows the imaginary part of the example pattern model at the sample plane.

FIG. 4B shows the real part of the complex amplitude and FIG. 4C shows the imaginary part. FIGS. 4B and 4C are a complete object plane representation of the pattern specifications. The whole pattern P is composed of a target set T at the center of the field and many surrounding patterns P. The target set T is composed of two separate square-shaped targets arranged in a box-in-box configuration. The sizes of the inner and outer targets are $1 \times 1$ μm$^2$ and $2 \times 2$ μm$^2$ respectively. The size of the clear area for target printing is $3 \times 3$ μm$^2$. Therefore, there is 0.5 μm clearance between the target and the surrounding patterns.

The inner target is composed of two overlapping subpatterns of slightly different sizes to model the finite side slope of a real target. The larger target is composed of six subpatterns, two overlapping subpatterns of slightly different sizes and four small partially overlapping subpatterns at the corners of the target pattern to model the corners of the real target more accurately. All the patterns and subpatterns are linearly superposed on each other. The example pattern shown here contains only a small number of subpatterns to make them clearly visible in the pictures. However, in real situations, each pattern can contain a very large number of subpatterns in order to make the model image agree with the real image accurately.

Ideally, the profiles of the targets are symmetric. However, in the real world, some asymmetry in the target profile is unavoidable. If the asymmetry is not modeled accurately, it can affect the accuracy of overlay measurement significantly. Therefore, the asymmetry in the target profile needs to be modeled with sufficient accuracy in order to achieve accurate overlay error measurements. The complex-amplitude-based target modeling adopted by the disclosure allows an accurate modeling of asymmetric profiles of targets.

Figure 5A:
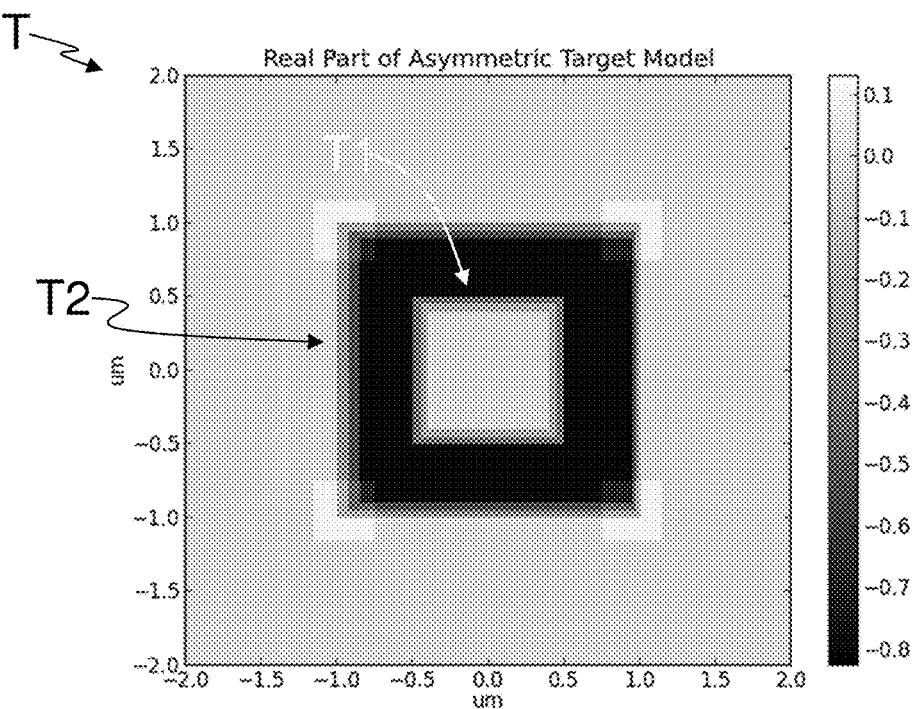
FIG. 5A shows the real part of an example asymmetric target model at the sample plane.
Figure 5B:
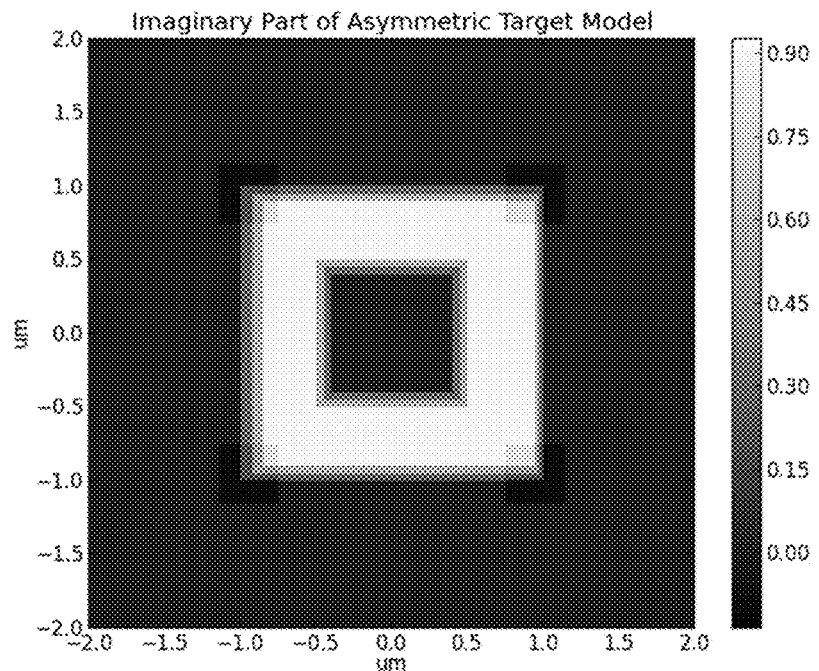
FIG. 5B shows the imaginary part of the example asymmetric target model at the sample plane.

FIGS. 5A and 5B show an example of the complex reflectance of an asymmetric target T. In this example, the target T includes an inner target T1 composed of three superimposed subpatterns and an outer target T2 composed of three large superimposed subpatterns and four corner decorators. All the patterns and subpatterns are linearly superposed on each other. The asymmetry is introduced in the left and right edges of the outer target T2 by shifting each of the large superimposed subpatterns slightly in the x-direction. The example asymmetric target model shown in FIGS. 5A and 5B is one of the simplest kinds. Much more complex asymmetric targets T can be generated by using more subpatterns p and also assigning a different amount of defocus to each subpattern. Asymmetry in the target T is just one example of target imperfection. There can be variety of other kinds of target imperfections. Any kind of reasonable target imperfection can be employed and modeled with sufficient accuracy.

The targets T shown in the example sample pattern P in FIGS. 5A and 5B are square-shaped. However, as stated previously, the target T can have any shape because the image of a pattern of any shape can be modeled accurately in the disclosure. Even a missing target is acceptable in the disclosure as long as some parts of the functional patterns can be used as targets. Thus, the systems and methods disclosed herein are completely flexible with respect to the design of target T.

As stated previously, the object plane representation cannot be accurate due to the finite sampling interval. It is important to remember that the object plane representation is not needed for image modeling in the disclosure. The object plane representation is only for visual explanatory purpose herein. Therefore, the inaccuracy of object plane representation is not relevant to image modeling.

Also as stated previously, model patterns are represented at the entrance pupil plane as a first step in the image modeling procedure. Actually, none of the sample plane representations of patterns presented herein is created directly. Rather, they are created by inverse Fourier transforming the entrance pupil representations of the patterns.

Figure 6A:
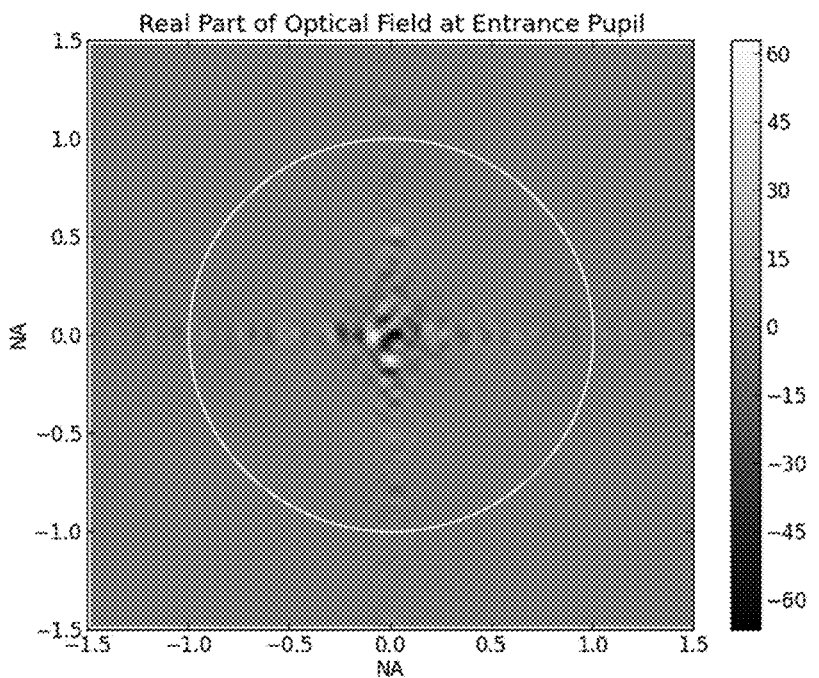
FIG. 6A shows the real part of the optical field at the entrance pupil plane for the pattern model shown in FIGS. 4A, 4B and 4C.
Figure 6B:
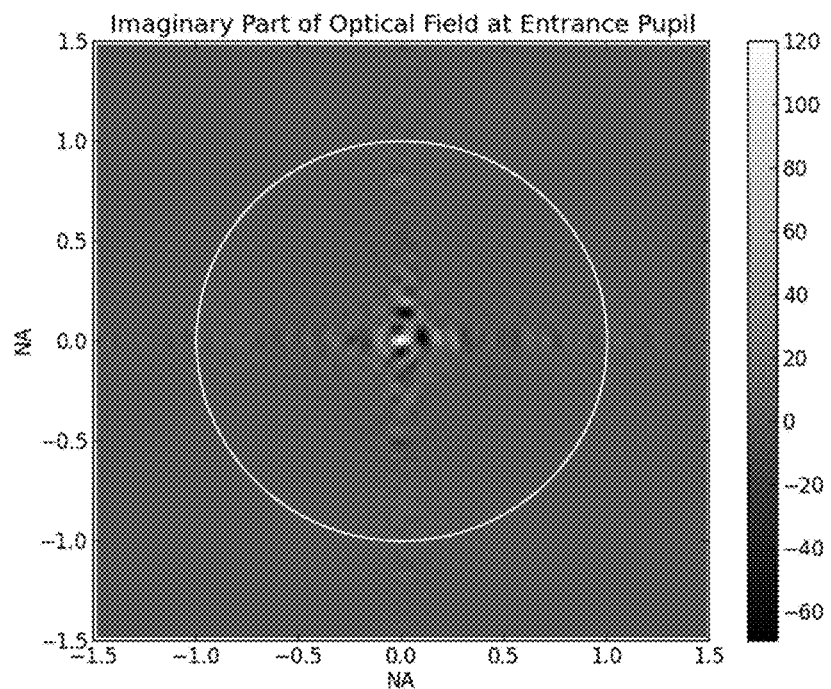
FIG. 6B shows the imaginary part of the optical field at the entrance pupil plane for the pattern model shown in FIGS. 4A, 4B and 4C.

FIGS. 6A and 6B respectively show the real and imaginary parts of the entrance pupil representation of the model pattern. As stated previously, the spatial frequency domain representation is obtained by analytically Fourier transforming each of the subpatterns p and summing the results. The spatial frequency coordinates are expressed in numerical aperture units which are 1/wavelength. The wavelength λ used is 0.658 μm.

FIGS. 6A and 6B show some energy outside the unit circle area whose boundary is shown with a white circular line. This energy is from the high spatial frequency components and belongs to evanescent waves and therefore cannot be collected by the imaging system 122. This means that the pattern model does not need to be accurate for this kind of high spatial frequency components. This is the origin of the tolerance in pattern or image modeling.

If a pattern is modeled properly, the majority of the modeling error, i.e., the difference between the model and the real pattern, happens at high frequency components, especially evanescent components. If we use a large number of subpatterns to depict the pattern accurately, even the evanescent components can be modeled accurately. However, this kind of extreme modeling accuracy is not needed because we can tolerate inaccuracies in the spatial frequency components that cannot be collected by the imaging system 122. The numerical aperture of imaging system 122 is not greater than 1.0. Therefore, a substantially amount of inaccuracy in the pattern modeling can be tolerated in a real overlay measurement system. This fact obviates the use of an extremely large number of subpatterns in pattern modeling, which leads to faster modeling and less computational resources. The use of a moderate number of subpatterns usually suffices in overlay measurements. This is especially true for the surrounding patterns which are more distant from the target than the width of the point spread function of the imaging system 122. These patterns do not require accurate modeling at all. Even a single subpattern for each pattern usually suffices.

The degree of accuracy needed in pattern modeling can be tested by comparing multiple overlay measurement results obtained with different pattern models having differing degrees of accuracy. If we want to model patterns quickly or minimize the computational resources required, it is a good idea to minimize the number of subpatterns used to model the patterns.

However, if we can spend more time for pattern modeling or have sufficient computational resources available, we can model the patterns with more accuracy than needed. This can waste some of the human and computational resources. But, this reduces the maximum error. Safety is important in most industrial applications. Therefore, overdoing the accuracy of pattern modeling is expected to be practiced extensively in many applications. As stated previously, the pattern modeling method allows not only moderately accurate modeling but also highly accurate modeling as well. Actually, the accuracy of pattern modeling can be indefinitely increased by using more and more subpatterns. This property of the modeling method is called asymptotic convergence of the model pattern to the actual pattern.

Figure 7A:
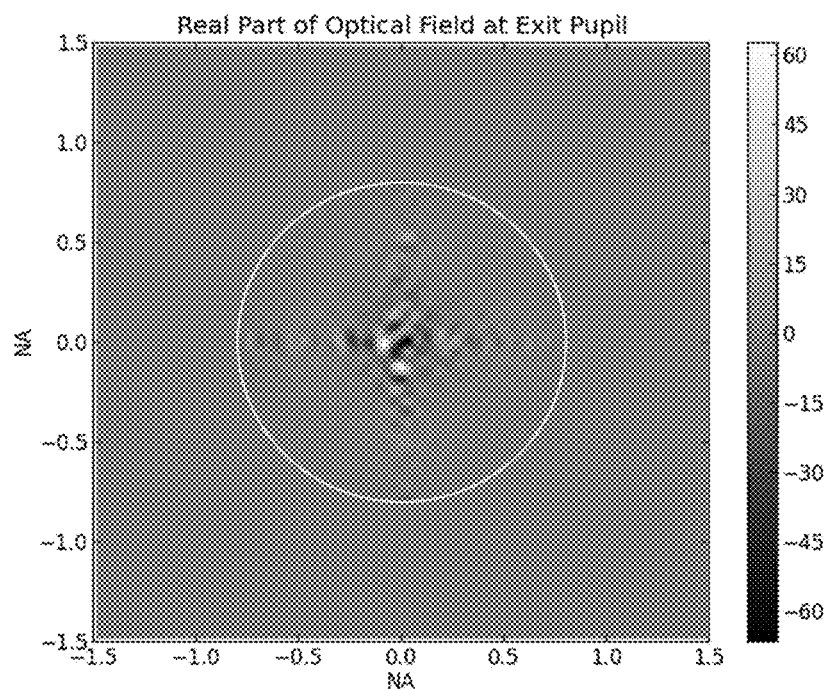
FIG. 7A shows the real part of the optical field at the exit pupil plane for the pattern model shown in FIGS. 4A, 4B and 4C.
Figure 7B:
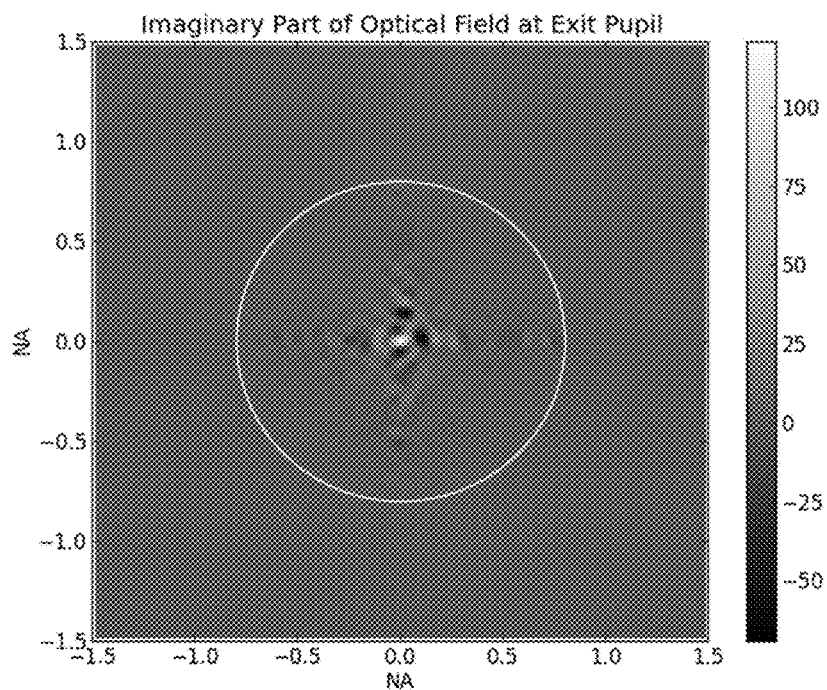
FIG. 7B shows the imaginary part of the optical field at the exit pupil plane for the pattern model shown in FIGS. 4A, 4B and 4C.

FIGS. 7A and 7B respectively show the real and imaginary parts of the complex amplitude of the optical field at the exit pupil as obtained by aperturing the entrance pupil representation shown in FIGS. 6A and 6B. The numerical aperture of the imaging system 122, which is indicated as a white circular line, is assumed to be 0.8. Consequently, all spatial frequency components higher than 0.8 are filtered out. Aberrations and distortion are assumed to be zero in this specific example. However, non-zero aberrations and distortion can be added precisely and easily to the pupil or the frequency domain representation of the optical field.

Figure 8A:
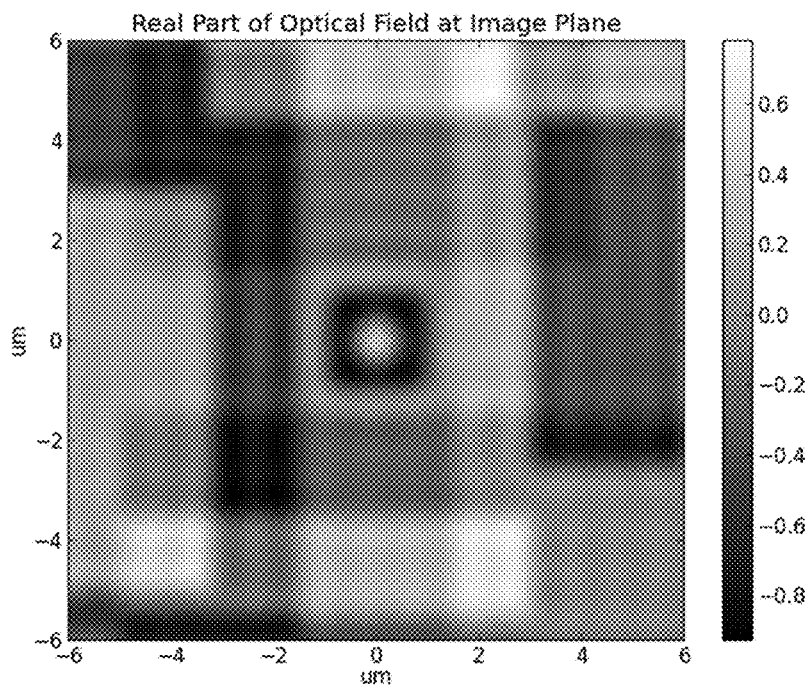
FIG. 8A shows the real part of the optical field at the image plane for the pattern model shown in FIGS. 4A, 4B and 4C.
Figure 8B:
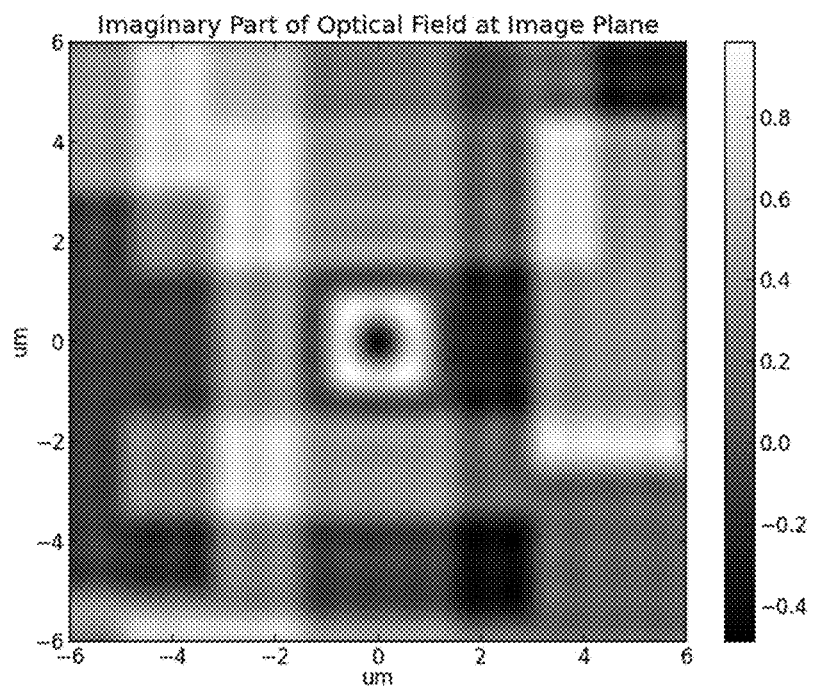
FIG. 8B shows the imaginary part of optical field at the image plane for the pattern model shown in FIGS. 4A, 4B and 4C.

FIGS. 8A and 8B respectively show the real and imaginary parts of the complex amplitude of the optical field at the image plane as obtained from FIGS. 7A and 7B by performing FFT on the complex amplitude of the optical field at the exit pupil. No phase is introduced to the specular component in this example image model. However, non-zero phase can be introduced to the specular component in a straightforward way as explained previously.

Figure 8C:
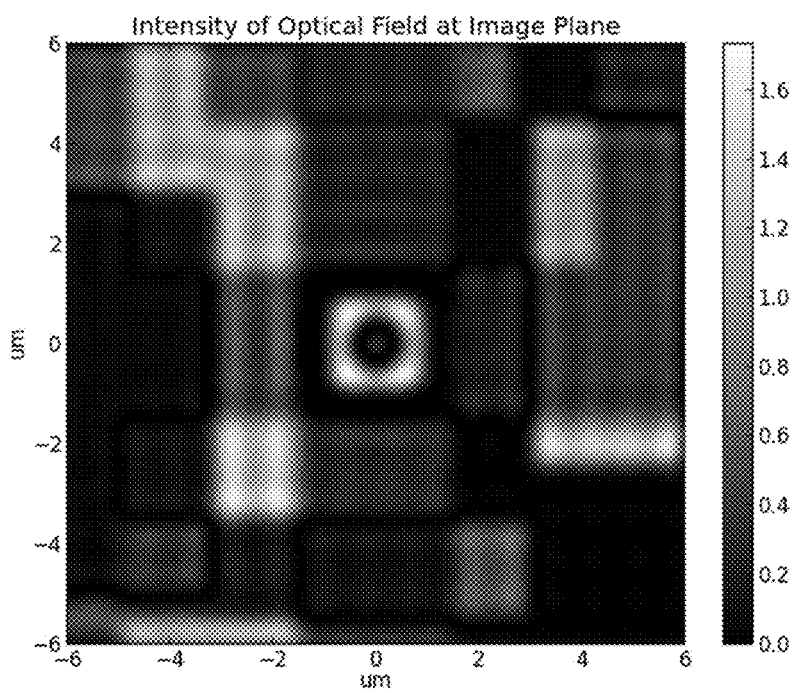
FIG. 8C shows the intensity of the optical field at the image plane for the pattern model shown in FIGS. 4A, 4B and 4C.

FIG. 8C shows the intensity of the image as obtained from FIGS. 8A and 8B. The image of FIG. 8C shows many interference fringes and blurred pattern boundaries. This means there is substantial inter-pattern interferences, which hinder a precise measurement of overlay error with existing overlay measurement systems and methods.

In order to filter out the inter-pattern interferences, the image needs to be modeled using the complex amplitude of the optical field. The systems and methods disclosed herein can measure the overlay error precisely even with lots of inter-pattern interferences because its model-based regressional image processing technique refines the image model automatically until the difference between model image and the measured image become negligible.

Figure 9:
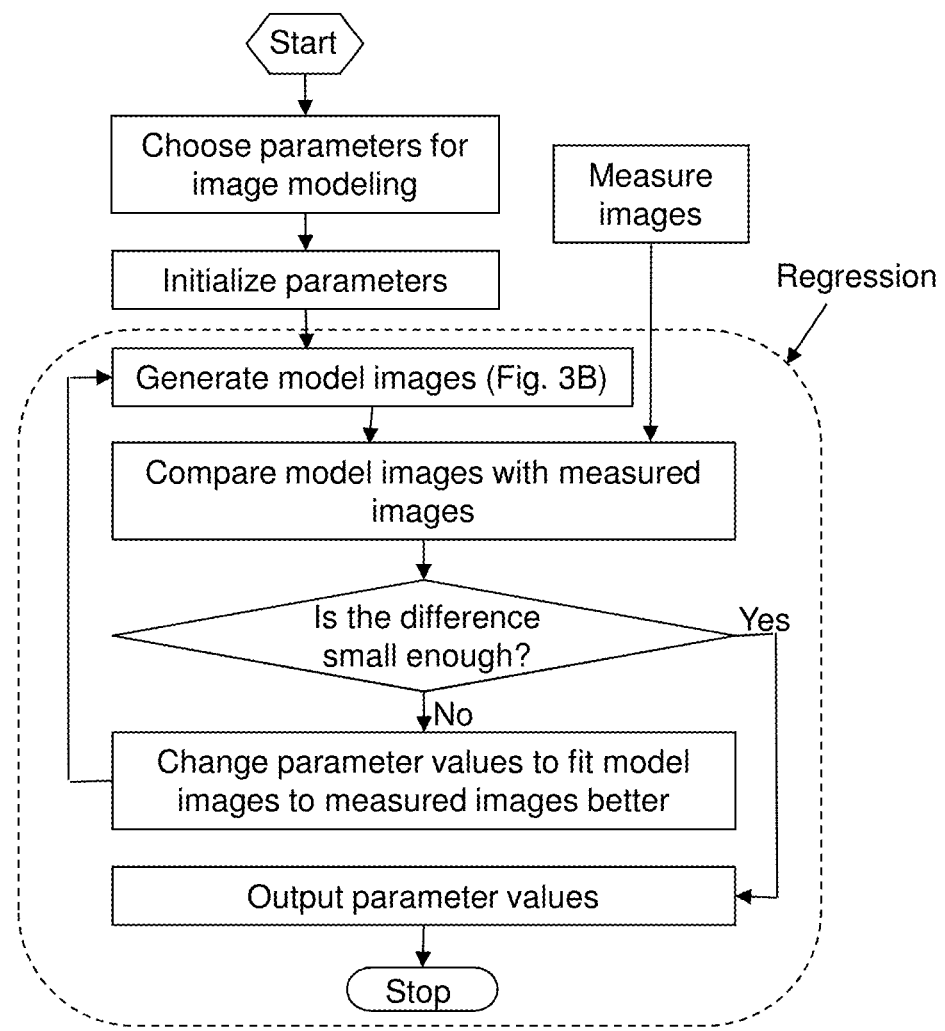
FIG. 9 shows the program flow of the model-based regressional image processing software.

The external and internal process flow of the method is shown in FIG. 9. Regression is an iterative fitting method. During regression, the image model is changed continuously until it fits the measured image. Change in the image model is achieved by changing the fitting parameters simultaneously in their desired directions. In this method, overlay error is one of the many fitting parameters. There are many different kinds of regression methods available. However, as stated previously, the Levenberg-Marquardt regression method is especially well-suited for overlay measurement. Regression methods usually require much more computing resources than simpler methods such as algebraic methods. However, the regression method combined with the complex-amplitude-based image modeling allows an accurate estimation of overlay error even in the presence of severe inter-pattern interferences.

It has been shown previously how the model-based regressional image processing method is used to determine the values of some pattern-related parameters needed for accurate image modeling. The same model-based regressional image processing method is used for the determination of overlay error. The only difference is the number of images used. As explained previously, the determination of parameter values needed for image modeling generally requires multiple images with different phase shifts to the specular component. But, the determination of overlay error generally requires only one image. This is because almost all the parameter values needed for image modeling are already determined and fixed when we run overlay the measurement and consequently only a small number of parameters need to be floating during the regression for determining the overlay error.

The regressional image processing process repeats the image modeling process iteratively varying floating parameters whose accurate values are unknown at the start of the regression. The regression continues until the floating parameter values reach their accurate values. The overlay parameter is one of floating parameters.

Figure 10A:
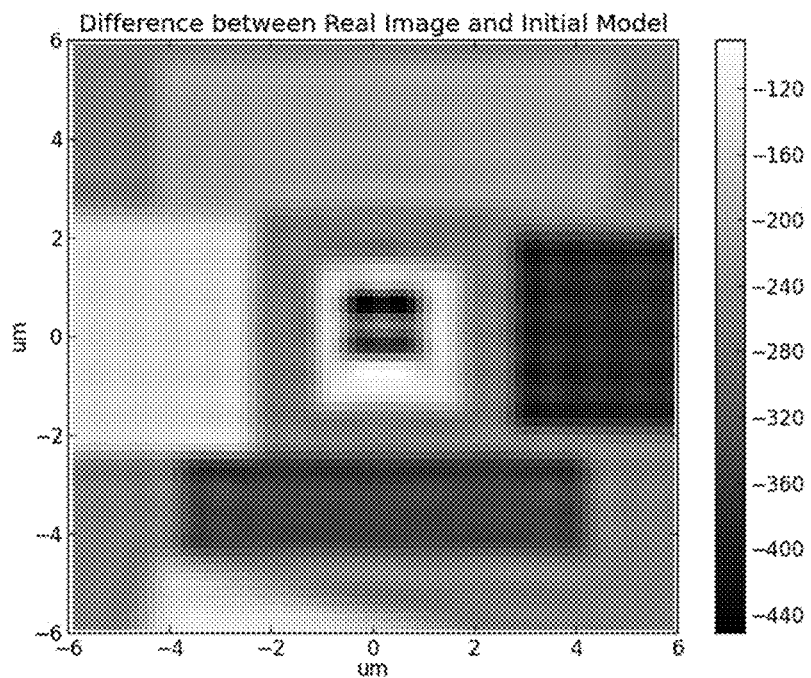
FIG. 10A shows the difference between an example real image and its model image at the beginning of the regressional image processing.

For example, FIG. 10A shows the difference between a real image and its model image at the start of the regressional image processing. It shows sizable differences between the real image and its model image due to some unavoidable inaccuracies in the initial image model at the beginning of the regression process. The unavoidable inaccuracies in the initial image model include the inaccuracies in the initial overlay errors, which were based on a best guess.

Figure 10B:
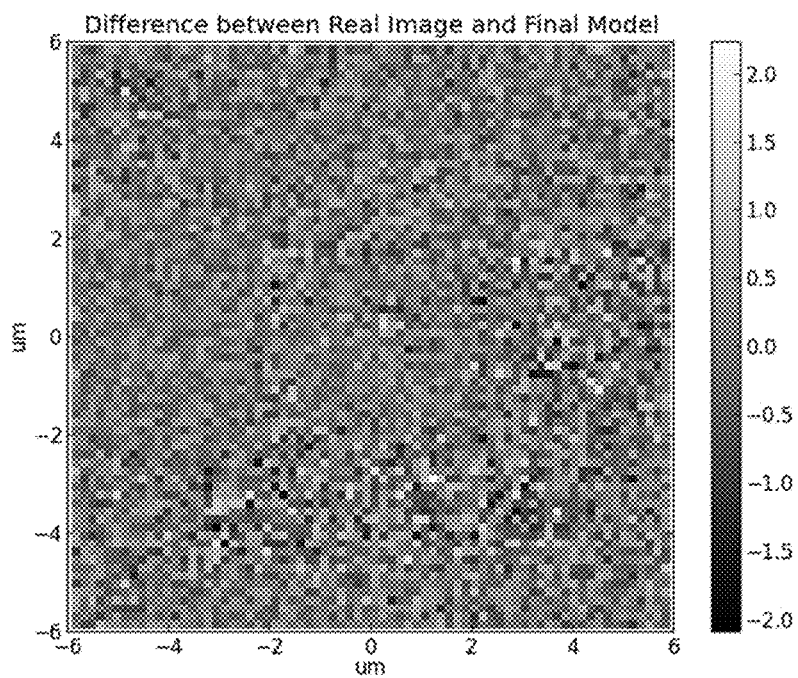
FIG. 10B shows the difference between the example real image and its model image at the end of a successful regressional image processing.

FIG. 10B shows the difference between the example real image and its model image at the end of a successful regressional image processing run. It shows the differences are tiny and very random. This means that the regression process varied all the floating parameter values in the image model appropriately to achieve a good agreement between the real image and the model image. As stated previously, overlay error is one of the floating parameters during the regression. Thus, regression determines the overlay errors and all other floating parameters simultaneously. In this case, the final image model established during the regression process represents the real measured image accurately. Consequently, the overlay error obtained this way is free from the interferences from other parameters. Thus, the systems and methods disclosed herein can determine overlay errors accurately even in the presence of surrounding patterns, aberrations, defocus, etc.

Figure 10C:
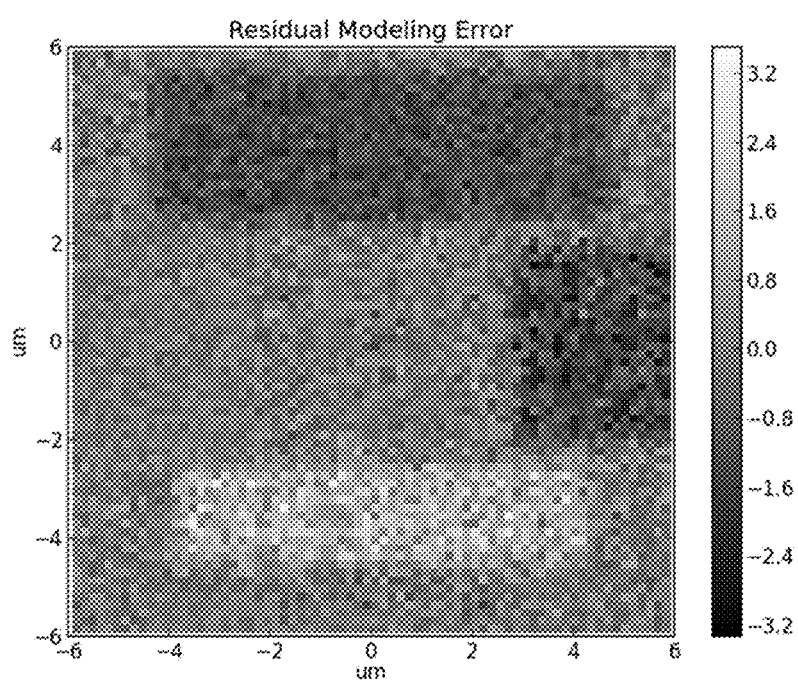
FIG. 10C shows sizable differences between the example real image and its model image when image modeling is not accurate.

FIG. 10C shows another example of the difference between a real image and its final model image after completion of the regressional image processing. FIG. 10C shows sizable non-random differences between the real image and its final model image. The differences are caused by the residual errors in the image model. In this case, the regression process failed to produce a well-matched model image and consequently it is highly likely that the overlay results are inaccurate. This indicates that the current image model is not accurate enough and therefore more elaborate modeling is needed.

Fortunately, FIG. 10C also shows which parts of the patterns are adequately modeled and which parts are not. This is the very information needed for troubleshooting. By taking multiple images of the sample with different relative phase values between the scattered and specular components and comparing the model images with the measured images, we can often pinpoint the areas of trouble. Thus, troubleshooting does not need to be done in blindfold or random fashion. The progress of troubleshooting can also be checked with the same method and the model can be refined until it is accurate enough.

Overlay errors are usually measured on the patterns on a sample 130 in the form of a wafer, which is usually mounted on a vacuum chuck. However, the wafer is eventually sliced into individual chips. The overlay errors we are truly interested in are those in the individual chips. This is because the overlay errors in an individual chip directly affect the chip's performance and reliability. The measured overlay errors and those in individual chip are usually the same. However, if there are sizable stresses in the process layers, the overlay errors in an individual chip can be different from measured overlay errors. This is because the slicing of wafer into individual chips usually releases some of the stresses in the process layers and the release of stresses can move some of the patterns in the chip slightly. Therefore, slight corrections to the measured overlay errors may be needed in order to determine the true overlay errors in the individual chips. For most applications, this kind of correction is a simple process, because the stress patterns are relatively simple and slowly varying across the wafer.

The new overlay measurement systems and methods disclosed herein provide all the features and functionalities needed for precise overlay measurements even in very adverse environments and conditions. The features and advantages of the disclosure are summarized below.

Features:
1. Control of relative phase between specular and scattered components. (Phase control of the specular component in the example system configuration.)
2. Complex-amplitude-based image modeling.
3. Pattern modeling in the spatial frequency domain.
4. Model-based regressional image processing.

Advantages:
1. Supports small targets for in-die overlay measurement.
2. Flexible target design.
3. Accurate handling of target asymmetry.
4. Weak signal handling capability.
5. Filtering of inter-pattern interferences.
6. Filtering of imaging system imperfections.
7. Larger tolerance on sample focus error.
8. Straightforward troubleshooting.

It will be apparent to those skilled in the art that various modifications and variations can be made to the present disclosure without departing from the spirit and scope of the disclosure. Thus it is intended that the present disclosure cover the modifications and variations of this disclosure provided they come within the scope of the appended claims and their equivalents.

What is claimed is:

1. A method of measuring an overlay error between first and second targets having respective actual first target parameters and actual second target parameters and that are respectively associated with first and second patterns that surround the first and second targets and that have respective actual first pattern parameters and actual second pattern parameters, the method comprising:
   a) illuminating the first and second targets to generate a scattered light component and a specular light component having a relative phase;
   b) using an imaging system having an image plane, capturing the scattered and specular light components at the image plane to form at least three images, wherein the relative phase is different for the at least three images;
   c) performing an analytical regression to determine from the at least three images a complex amplitude of an optical field of the scattered light component at the image plane;
   d) using the complex amplitude of the optical field of the scattered light component to obtain estimated first and second target parameters and estimated first and second pattern parameters;
   e) performing a first numerical regression using an image model of the imaging system, including inputting into the image model the estimated first and second target parameters and the estimated first and second pattern parameters to generate a modeled image, wherein the first numerical regression iteratively compares the modeled image to the measured image and modifies the estimated first and second target parameters and the estimated first and second pattern parameters to minimize a difference between the modeled image and the measured image to determine the actual first and second target parameters and the actual first and second pattern parameters;
   f) determining an optimum phase shift from the actual first and second target parameters;
   g) capturing an image of the first and second targets using the optimum phase; and
   h) performing a second numerical regression using the image model and the image captured in act g) to determine a relative position between the first and second targets that defines the overlay error.

2. The method of claim 1, wherein the illuminating of the first and second targets is through at least a portion of the imaging system.

3. The method of claim 1, wherein the illuminating of the first and second targets is through at least a portion of a substrate that supports the first and second targets.

4. The method of claim 1, further comprising using at least three different phase-shifters operably arranged in the imaging system to define the different relative phases for the at least three images.

5. The method of claim 1, wherein the first and second targets and first and second patterns occupy an area on the sample of 100 $\mu m^2$ or less.

6. The method of claim 1, wherein the image model includes at least one aberration of the imaging system.

7. The method of claim 1, wherein the estimated first and second target parameters each includes at least one of: size, shape, complex reflectance and defocus.

8. The method of claim 1, wherein at least a portion of the image model is defined in a spatial frequency or pupil plane domain, and a least a portion of the first numerical regression is carried out in the frequency or pupil plane domain.

9. The method of claim 1, wherein first and second numerical regressions are carried out in a computer based on instructions embodied in a non-transitory computer-readable medium.

10. The method of claim 1, further comprising:
    decomposing the first and second patterns into respective first and second sub-patterns;
    converting the first and second sub-patterns into respective first and second frequency domain representations; and
    processing the first and second frequency domain representations of the first and second sub-patterns to construct the image model.

11. A method of measuring an overlay error between first and second targets respectively surrounded by first and second patterns, the method comprising:
    a) using an imaging system having an image plane, capturing at the image plane three images, with each image based on a scattered light component and a specular light component from the first and second targets, wherein for each image the scattered and specular light components have a relative phase, and wherein the relative phase is different for the three images;
    b) using the three images to define a complex amplitude of the optical field of the scattered light component;
    c) using the complex amplitude of the optical field of the scattered light component to obtain estimated: i) first target parameters; ii) second target parameters; iii) first pattern parameters; and iv) second pattern parameters;
    d) using an image model of the imaging system to generate a modeled image based on the estimated first target parameters, the estimated second target parameters, the estimated first pattern parameters, and the estimated second pattern parameters;
    e) determining actual first target parameters, actual second target parameters, actual first pattern parameters, and actual second pattern parameters that minimize a difference between the modeled image and the measured image;
    g) capturing an image of the first and second targets and the first and second patterns using the imaging system configured to impart the optimum relative phase; and
    h) determining a relative position between the first and second targets that defines the overlay error using the image model and the image captured in act g).

12. The method of claim 11, further including illuminating the first and second targets through at least a portion of the imaging system to form the scattered light components and specular light components from the first and second targets.

13. The method of claim 11, further comprising using at least three different phase-shifters operably arranged in the imaging system to define the different relative phases for the three images.

14. The method of claim 11, wherein the first and second targets and first and second patterns occupy an area on the sample of 100 $\mu m^2$ or less.

15. The method of claim 11, wherein the image model includes at least one aberration of the imaging system.

16. The method of claim 11, wherein first and second estimated target parameters each includes at least one of: size, shape, complex reflectance and defocus.

17. The method of claim 11, wherein at least a portion of the image model is defined in a frequency domain, and a least a portion of act e) includes performing a numerical regression carried in the frequency domain.

18. The method of claim 11, wherein acts e) and h) are carried out in a computer based on instructions embodied in a non-transitory computer-readable medium.

19. The method of claim 11, further comprising:
   decomposing the first and second patterns into respective first and second sub-patterns;
   converting the first and second sub-patterns into respective first and second frequency domain representations; and
   processing the first and second frequency domain representations of the first and second sub-patterns.

20. A method of measuring an overlay error between first and second targets having respective actual first target parameters and actual second target parameters and that are respectively associated with first and second patterns having respective actual first pattern parameters and actual second pattern parameters, the method comprising:
   a) illuminating the first and second targets to generate a scattered light component and a specular light component having a relative phase;
   b) using an imaging system having an image plane, capturing at the image plane at least three images of the combined scattered and specular light components, wherein the relative phase is different for the at least three images;
   c) performing an analytical regression to determine from the at least three images a complex amplitude of an optical field of the scattered light component at the image plane;
   d) using the complex amplitude of the optical field of the scattered light component to obtain estimated first and second target parameters and estimated first and second pattern parameters;
   e) performing a first numerical regression using an image model that takes into account the imaging system characteristics to approximate the image formed in the imaging system, including inputting into the image model the estimated first and second target parameters and the estimated first and second pattern parameters to generate a modeled image, wherein the first numerical regression iteratively compares the modeled image to the measured image and modifies the estimated first and estimated second target parameters and estimated first and estimated second pattern parameters to minimize a difference between the modeled image and the measured image to determine the actual first and second target parameters and the actual first and second pattern parameters;
   f) capturing an image of the first and second targets and first and second patterns using the imaging system configured to block the specular component; and
   g) performing a second numerical regression using the image model and the image captured in act f) to determine a relative position between the first and second targets that defines the overlay error.

21. A method of measuring an overlay error between first and second targets having respective actual first target parameters and actual second target parameters and that are respectively associated with first and second patterns that surround the first and second targets and that have respective actual first pattern parameters and actual second pattern parameters, the method comprising:
   a) illuminating the first and second targets to generate a scattered light component;
   b) using an imaging system having an image plane, capturing at the image plane an image of the scattered component by blocking the specular component;
   c) estimating the complex amplitude of an optical field of the scattered light component at the image plane;
   d) using the complex amplitude of the optical field of the scattered light component to obtain estimated first and second target parameters and estimated first and second pattern parameters;
   e) performing a first numerical regression using an image model of the imaging system, including inputting into the image model the estimated first and second target parameters and the estimated first and second pattern parameters to generate a modeled image, wherein the first numerical regression iteratively compares the modeled image to the measured image and modifies the estimated first and second target parameters and estimated first and second pattern parameters to minimize a difference between the modeled image and the measured image to determine the actual first and second target parameters and the actual first and second pattern parameters; and
   f) performing a second numerical regression using the image model and the image captured in act b) to determine a relative position between the first and second targets that defines the overlay error.

* * * * *